(12) United States Patent
Kubo

(10) Patent No.: US 12,318,071 B2
(45) Date of Patent: Jun. 3, 2025

(54) ENDOSCOPE SYSTEM AND METHOD OF OPERATING ENDOSCOPE SYSTEM

(71) Applicant: FUJIFILM Corporation, Tokyo (JP)

(72) Inventor: Masahiro Kubo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 416 days.

(21) Appl. No.: 17/822,348

(22) Filed: Aug. 25, 2022

(65) Prior Publication Data

US 2022/0400930 A1 Dec. 22, 2022

Related U.S. Application Data

(63) Continuation of application No. PCT/JP2021/005937, filed on Feb. 17, 2021.

(30) Foreign Application Priority Data

Feb. 28, 2020 (JP) ................. 2020-034275

(51) Int. Cl.
*A61B 1/06* (2006.01)
*A61B 1/00* (2006.01)

(52) U.S. Cl.
CPC ........ *A61B 1/0655* (2022.02); *A61B 1/00006* (2013.01); *A61B 1/00009* (2013.01);
(Continued)

(58) Field of Classification Search
CPC .............. A61B 1/0655; A61B 1/00006; A61B 1/00009; A61B 1/0002; A61B 1/0005;
(Continued)

(56) References Cited

U.S. PATENT DOCUMENTS 5,896,166 A * 4/1999 D'Alfonso ............. H04N 23/66
348/E5.043
8,723,965 B2 5/2014 Ishii et al.
(Continued)

FOREIGN PATENT DOCUMENTS

EP 3 708 063 A1 9/2020
JP H03-016470 A 1/1991
(Continued)

OTHER PUBLICATIONS

An Office Action; "Notice of Reasons for Refusal," mailed by the Japanese Patent Office on Jul. 25, 2023, which corresponds to Japanese Patent Application No. 2022-503290 and is related to U.S. Appl. No. 17/822,348; with English language translation.
(Continued)

*Primary Examiner* — Anh Tuan T Nguyen
*Assistant Examiner* — Jae Woo
(74) *Attorney, Agent, or Firm* — Studebaker Brackett PLLC

(57) ABSTRACT

A first illumination light beam is switched to a second illumination light beam and the second illumination light beam is emitted for a period of at least one frame, during a period in which the first illumination light beam is emitted. A first image or a second image obtained by imaging an observation target illuminated with the first illumination light beam or the second illumination light beam is acquired for each frame. At least one first image and at least one second image that satisfy a preset selection condition are selected and stored from a plurality of the first images and a plurality of the second images acquired in a preset period prior to a time of a processing start operation of image storage processing.

11 Claims, 18 Drawing Sheets

(52) U.S. Cl.
CPC .......... *A61B 1/0002* (2013.01); *A61B 1/0005* (2013.01); *A61B 1/0638* (2013.01); *A61B 1/0669* (2013.01); *A61B 1/0684* (2013.01)

(58) Field of Classification Search
CPC .. A61B 1/0669; A61B 1/0684; G02B 23/2461
See application file for complete search history.

(56) References Cited

U.S. PATENT DOCUMENTS

| | | | |
|---|---|---|---|
| 2009/0289200 A1 | 11/2009 | Ishii | |
| 2013/0058573 A1* | 3/2013 | Suzuki | A61B 1/045 382/167 |
| 2013/0245411 A1* | 9/2013 | Saito | A61B 1/000094 600/339 |
| 2013/0271587 A1* | 10/2013 | Tsuyuki | A61B 1/051 348/71 |
| 2014/0002627 A1* | 1/2014 | Tashiro | A61B 8/56 348/71 |
| 2014/0066784 A1* | 3/2014 | Yokota | A61B 1/0655 600/476 |
| 2014/0171737 A1* | 6/2014 | Kagaya | H04N 25/531 600/109 |
| 2015/0272429 A1* | 10/2015 | Shigeta | A61B 1/0002 348/65 |
| 2017/0164819 A1* | 6/2017 | Bai | A61B 1/00096 |
| 2017/0290496 A1* | 10/2017 | Fukuda | G02B 23/2453 |
| 2019/0008361 A1* | 1/2019 | Imai | G06T 5/73 |
| 2020/0015656 A1* | 1/2020 | Tsuyuki | A61B 1/051 |
| 2020/0138275 A1* | 5/2020 | Homma | G06T 7/0012 |
| 2020/0260933 A1* | 8/2020 | Kubo | A61B 1/0638 |
| 2020/0260942 A1 | 8/2020 | Kubo | |
| 2020/0268237 A1* | 8/2020 | Kobayashi | A61B 1/041 |
| 2020/0305700 A1* | 10/2020 | Kamon | A61B 1/045 |
| 2023/0000308 A1* | 1/2023 | Iwane | A61B 1/0638 |
| 2023/0029239 A1* | 1/2023 | Tsujimoto | A61B 1/0646 |
| 2023/0037060 A1* | 2/2023 | Shimomura | G02B 23/26 |

FOREIGN PATENT DOCUMENTS

| | | |
|---|---|---|
| JP | 2009-279171 A | 12/2009 |
| JP | 2010-279454 A | 12/2010 |
| JP | 2013-188364 A | 9/2013 |
| JP | 6499050 B2 | 5/2014 |
| JP | 2014-220690 A | 11/2014 |
| JP | 2016-123576 A | 7/2016 |
| JP | 2017-079870 A | 5/2017 |
| JP | 2017-164393 A | 9/2017 |
| WO | 2019/093256 A1 | 5/2019 |
| WO | 2019/093355 A1 | 5/2019 |
| WO | 2019/163540 A1 | 8/2019 |

OTHER PUBLICATIONS

International Search Report issued in PCT/JP2021/005937; mailed Apr. 20, 2021.

International Preliminary Report On Patentability (Chapter I) and Written Opinion of the International Searching Authority issued in PCT/JP2021/005937; issued Aug. 30, 2022.

The extended European search report issued by the European Patent Office on Jul. 6, 2023, which corresponds to European Patent Application No. 21761328.0-1126 and is related to U.S. Appl. No. 17/822,348.

An Office Action mailed by China National Intellectual Property Administration on Mar. 6, 2025, which corresponds to Chinese Patent Application No. 202180017252.3 and is related to U.S. Appl. No. 17/822,348; with English language translation.

* cited by examiner

ENDOSCOPE SYSTEM AND METHOD OF OPERATING ENDOSCOPE SYSTEM

CROSS-REFERENCE TO RELATED APPLICATIONS

This application is a Continuation of PCT International Application No. PCT/JP2021/005937 filed on 17 Feb. 2021, which claims priority under 35 U.S.C. § 119(a) to Japanese Patent Application No. 2020-034275 filed on 28 Feb. 2020. The above application is hereby expressly incorporated by reference, in its entirety, into the present application.

BACKGROUND OF THE INVENTION

1. Field of the Invention

The present invention relates to an endoscope system that stores a plurality of types of still images through an instruction, and a method of operating the endoscope system.

2. Description of the Related Art

In the medical field, a diagnosis using an endoscope system, which comprises a light source device, an endoscope, and a processor device, has been widely performed. In the diagnosis using the endoscope system, various types of information regarding a surface structure of an observation target, a mucous membrane surface layer, or the like may be obtained by using an image (hereinafter, referred to as an endoscopic image) obtained by imaging the observation target with the endoscope through image-enhanced observation (IEE, image enhanced endoscopy) in which an illumination light beam or the like is devised.

In the diagnosis using IEE, an appropriate diagnosis may be made by acquiring a plurality of types of images obtained by a plurality of types of illumination light beams and the like, and comparing in detail or superimposing these images. As an endoscope system that uses a plurality of types of images including a normal image obtained through white light observation, an image obtained through IEE, and the like, an endoscope system that displays an oxygen saturation observation moving image, a normal observation moving image, and a blood vessel-enhanced observation moving image in parallel on a display device, and that sets an exposure condition and then stores each observation moving image as a still image in a case where a freeze button is operated while the moving images are displayed, and the like are disclosed (JP2013-188364A, corresponding to US2013/0245411A1).

SUMMARY OF THE INVENTION

In the related art, a plurality of types of still images with less blur are selected and stored, for example, at a point in time back to the past by a certain period from a point in time when an instruction to store the still image is given by the operation of the freeze button while the moving image is displayed. In a plurality of illumination light beams, for example, two types of images are compared: an image using the illumination light beam that is used to enhance superficial blood vessels or the like of the observation target and an image using the illumination light beam that is used to enhance medium-depth blood vessels or the like of the same observation target so that information on the depth direction of the observation target can be obtained, which is effective, for example, in a case where a diagnosis on the extent of a lesion is performed.

In order to store a plurality of types of still images corresponding to a plurality of illumination light beams, for example, as in the related art, the illumination light beams are switched and the still image is stored for each illumination light beam, whereby various still images are stored. In a case where an observation target is observed and an image thereof is picked up while the plurality of illumination light beams are repeatedly switched, it is preferable that the switching cycle between the illumination light beams used for observation is as long as possible due to problems, such as photosensitivity. However, in this case, it is necessary to select an image of an illumination light beam that is not used for observation when a still image acquisition instruction is given, and the longer the switching cycle between the illumination light beams is, the larger the difference in time between the plurality of types of stored images is. Since the larger the difference in time between the plurality of types of stored images is, the higher the probability that the positional deviation between the images may occur significantly is due to the motion of the observation target and the like, there is a concern that still images unsuitable for comparison or superimposition may be stored.

On the other hand, in order to reduce the difference in time between the plurality of types of stored images, it is conceivable to reduce the switching cycle between the plurality of types of illumination light beams to shorten the illumination time of each illumination light beam. However, there is a concern that this method may cause problems, such as light flicker or photosensitivity, which is a trade-off with the difference in time between images.

Further, in JP2013-188364A, in addition to the above, a plurality of types of illumination light beams are automatically switched in a predetermined order, and moving images corresponding to the respective illumination light beams are simultaneously displayed on a display. In this case, a frame rate in a case of one illumination light beam is equal to or less than half that of a case where illumination light beams are not switched, and it may be difficult to diagnose, for example, the observation target that may move, through comparison or superimposition between the plurality of types of images.

The present invention has been made in view of the above circumstances, and an object thereof is to provide an endoscope system that stores a plurality of types of still images in a state suitable for comparison or superimposition, through a single instruction, and a method of operating the endoscope system.

The present invention relates to an endoscope system comprising a plurality of semiconductor light sources that emit light beams having wavelength bands different from each other, a light source processor, and an image processor. The light source processor performs control to switch a first illumination light beam to a second illumination light beam of which a combination of light intensity ratios between the plurality of semiconductor light sources is different from the first illumination light beam, to emit the second illumination light beam for a period of at least one frame, during a first period in which the first illumination light beam, out of a plurality of illumination light beams of which combinations of the light intensity ratios are different from each other, is emitted. The image processor acquires a first image or a second image obtained by imaging an observation target illuminated with the first illumination light beam or the second illumination light beam, for each frame, performs image storage processing of storing the first image and the second image, and selects and stores at least one first image and at least one second image that satisfy a preset selection condition, from a plurality of the first images and a plurality of the second images acquired in a preset period prior to a time of a processing start operation for starting the image storage processing, in a case where the processing start operation is performed.

It is preferable that the selection condition is that a first image and a second image having least blur, out of the plurality of acquired first images and the plurality of acquired second images, are selected.

It is preferable that the selection condition is that a first image and a second image having a smallest positional deviation between the first image and the second image selected from the plurality of acquired first images and the plurality of acquired second images are selected.

It is preferable that the selection condition is that a first image and a second image having a smallest difference in acquisition time between the first image and the second image selected from the plurality of acquired first images and the plurality of acquired second images are selected.

It is preferable that the light source processor alternately repeats the first period and a second period in which the second illumination light beam is emitted, and performs control to switch the second illumination light beam to the first illumination light beam to emit the first illumination light beam for a period of at least one frame during the second period.

It is preferable that the image processor performs control to display the acquired first image and/or the acquired second image, on a display, and displays at least the second image on the display during the second period.

It is preferable that the image processor performs control to display the acquired first image and/or the acquired second image, on a display, and displays at least the first image on the display during the first period.

It is preferable that the semiconductor light sources include a first semiconductor light source that emits a first narrow-band light beam having a wavelength band of which a central wavelength is 410±10 nm and a wavelength range is 380 to 420 nm, and a second semiconductor light source that emits a second narrow-band light beam having a wavelength band of which a central wavelength is 450±10 nm and a wavelength range is 420 to 500 nm.

It is preferable that the image processor stores the first image and the second image after adding information regarding the illumination light beams used.

Further, the present invention relates to a method of operating an endoscope system including a plurality of semiconductor light sources that emit light beams having wavelength bands different from each other, a light source processor, and an image processor. The method comprises performing, by the light source processor, control to switch a first illumination light beam to a second illumination light beam of which a combination of light intensity ratios between the plurality of semiconductor light sources is different from the first illumination light beam, to emit the second illumination light beam for a period of at least one frame, during a first period in which the first illumination light beam, out of a plurality of illumination light beams of which combinations of the light intensity ratios are different from each other, is emitted. The method comprises acquiring, by the image processor, a first image or a second image obtained by imaging an observation target illuminated with the first illumination light beam or the second illumination light beam, for each frame; performing, by the image processor, image storage processing of storing the first image and the second image; and selecting and storing, by the image processor, at least one first image and at least one second image that satisfy a preset selection condition, from a plurality of the first images and a plurality of the second images acquired in a preset period prior to a time of a processing start operation for starting the image storage processing, in a case where the processing start operation is performed.

According to the present invention, it is possible to store a plurality of types of still images in a state suitable for comparison or superimposition, through a single instruction.

DESCRIPTION OF THE PREFERRED EMBODIMENTS

Figure 1:
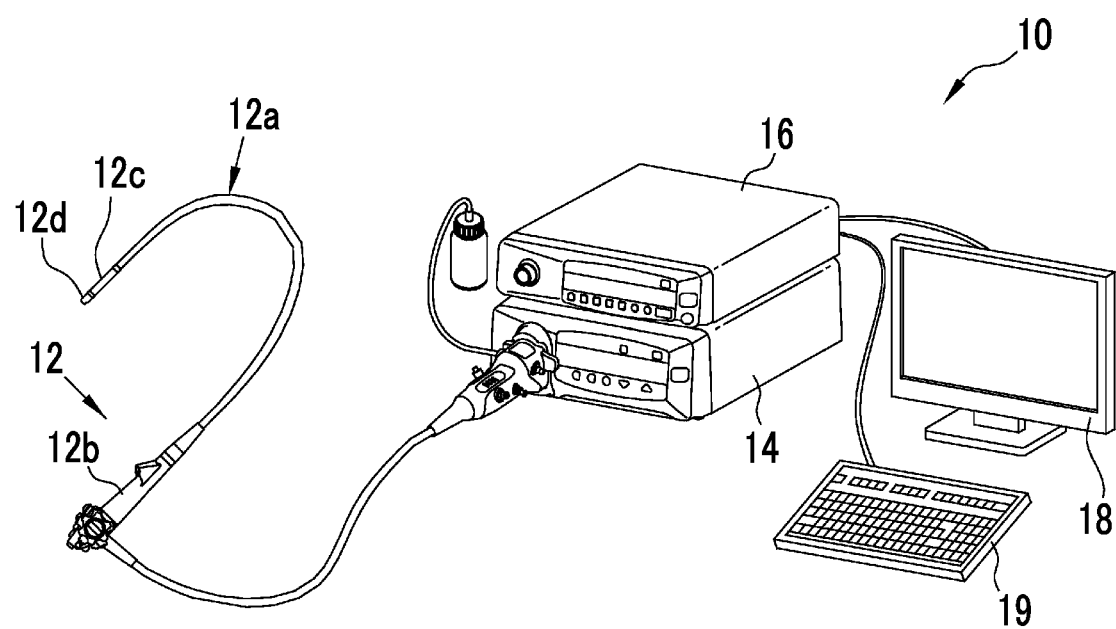
FIG. 1 is an external view of an endoscope system.

In FIG. 1, an endoscope system 10 includes an endoscope 12, a light source device 14, a processor device 16, a display 18, and a keyboard 19. The endoscope 12 is optically connected to the light source device 14 and is electrically connected to the processor device 16. The endoscope 12 includes an insertion part 12a inserted into a body of an observation target, an operation part 12b provided at the proximal end portion of the insertion part 12a, and a bendable portion 12c and a distal end portion 12d that are provided in the insertion part 12a on the distal end side. The bendable portion 12c is bent by the operation of an angle knob 12e (see FIG. 2) of the operation part 12b. The bendable portion 12c is bent so that the distal end portion 12d faces a desired direction.

Figure 2:
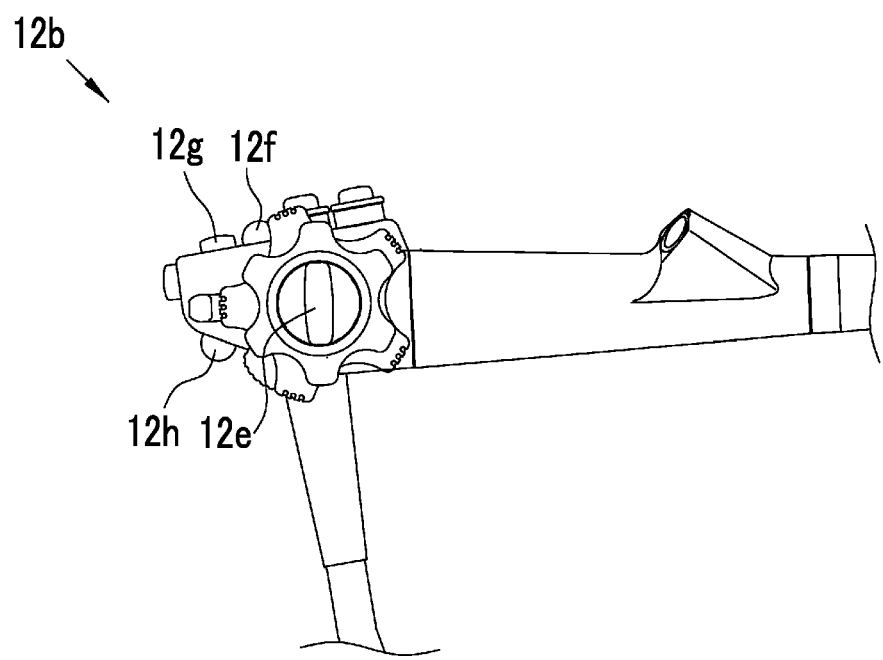
FIG. 2 is an external view of an operation part of an endoscope.

As shown in FIG. 2, the operation part 12b includes a mode changeover switch 12g used for an observation mode switching operation, a zoom operation portion 12h that is used to change an image pickup magnification, and a still image acquisition instruction portion 12f through which a still image acquisition instruction is given, in addition to the angle knob 12e. An operation or an instruction using the keyboard 19, a foot switch (not shown), or the like, in addition to the mode changeover switch 12g or a scope switch of the still image acquisition instruction portion 12f, may be used for the observation mode switching operation, the zoom operation, or the still image acquisition instruction.

The endoscope system 10 has three modes, that is, a normal observation mode, a special observation mode, and a multi-observation mode. The normal observation mode is a mode for displaying a normal observation image (hereinafter, referred to as a normal image), which is an image with natural color tones obtained by picking up an image of the observation target using white light as an illumination light beam, on the display 18. The special observation mode includes a first special observation mode and a second special observation mode. The first special observation mode is a mode for displaying a first special observation image (hereinafter, referred to as a first image) in which surface layer information such as a superficial blood vessel is enhanced, on the display 18, and the second special observation mode is a mode for displaying a second special observation image (hereinafter, referred to as a second image) in which deep layer information such as a deep blood vessel is enhanced, on the display 18. The multi-observation mode is a mode for automatically switching between the first special observation mode and the second special observation mode.

The processor device 16 is electrically connected to the display 18 and the keyboard 19. The display 18 outputs and displays, for example, the normal image, the first image, the second image, and/or accessory information on these images. The keyboard 19 functions as a user interface that receives an input operation, such as function settings. An external recording unit (not shown) that records images, image information, or the like may be connected to the processor device 16.

Figure 3:
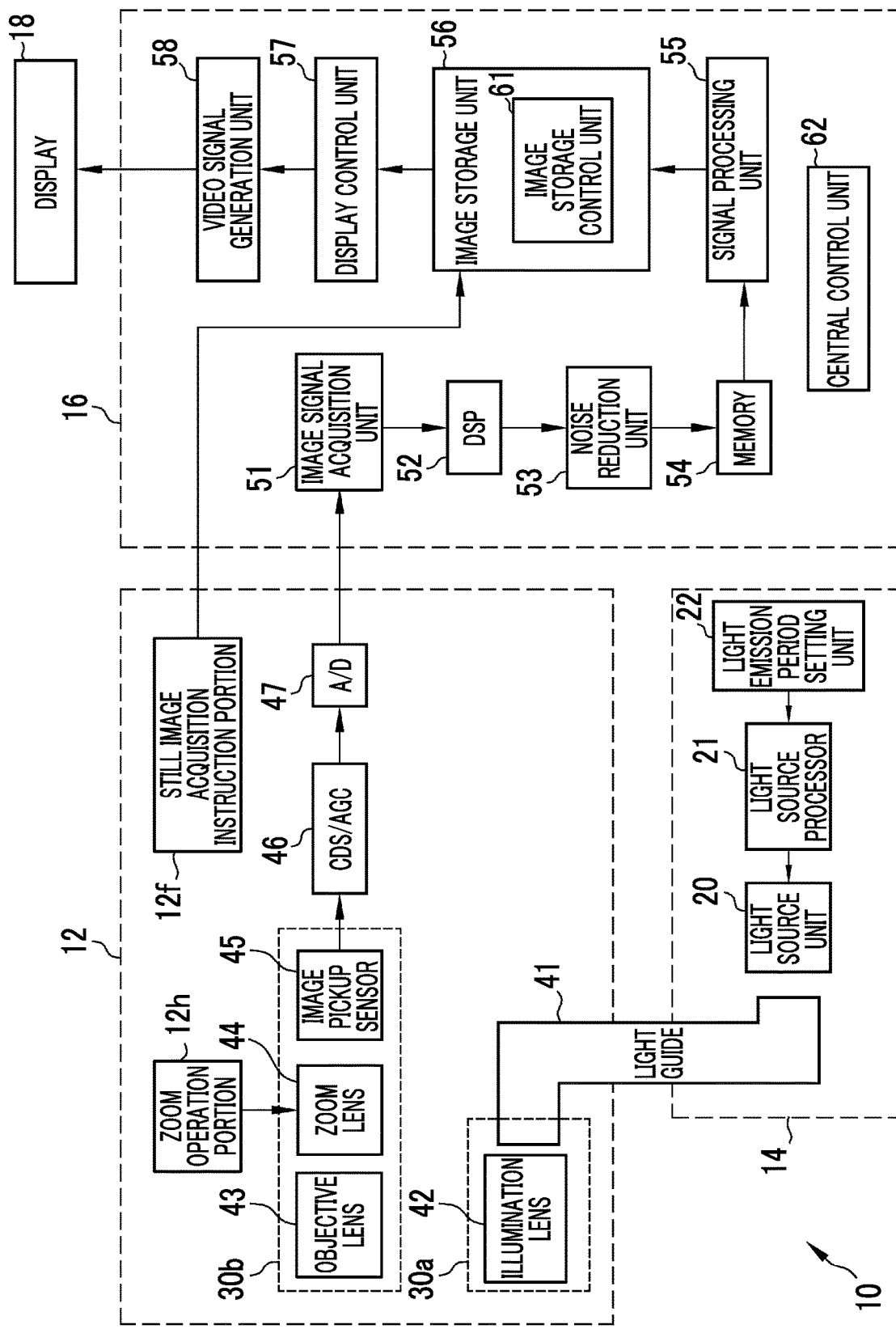
FIG. 3 is a block diagram showing a function of the endoscope system.

In FIG. 3, the light source device 14 is a device that emits illumination light beams with which the observation target is irradiated, and comprises a light source unit 20 and a light source processor 21 that controls the light source unit 20. The light source unit 20 is composed of, for example, a semiconductor light source, such as a multi-color light emitting diode (LED), a combination of a laser diode and a phosphor, or a xenon lamp or halogen light source. In addition, the light source unit 20 includes, for example, an optical filter that is used to adjust the wavelength band of a light beam emitted by the LED or the like. The light source processor 21 turns on/off each LED or the like or adjusts the drive current and drive voltage of each LED or the like, thereby controlling the amount of the illumination light beam. Further, the light source processor 21 controls the wavelength band of the illumination light beam by changing the optical filter or the like.

Figure 4:
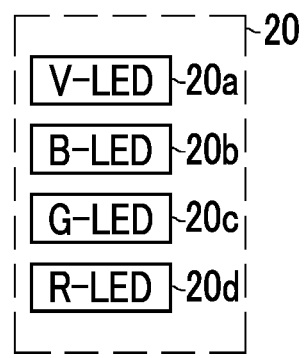
FIG. 4 is a diagram illustrating four-color LEDs provided in a light source unit.

As shown in FIG. 4, in the present embodiment, the light source unit 20 has four-color LEDs, that is, a violet light emitting diode (V-LED) 20a, a blue light emitting diode (B-LED) 20b, a green light emitting diode (G-LED) 20c, and a red light emitting diode (R-LED) 20d.

Figure 5:
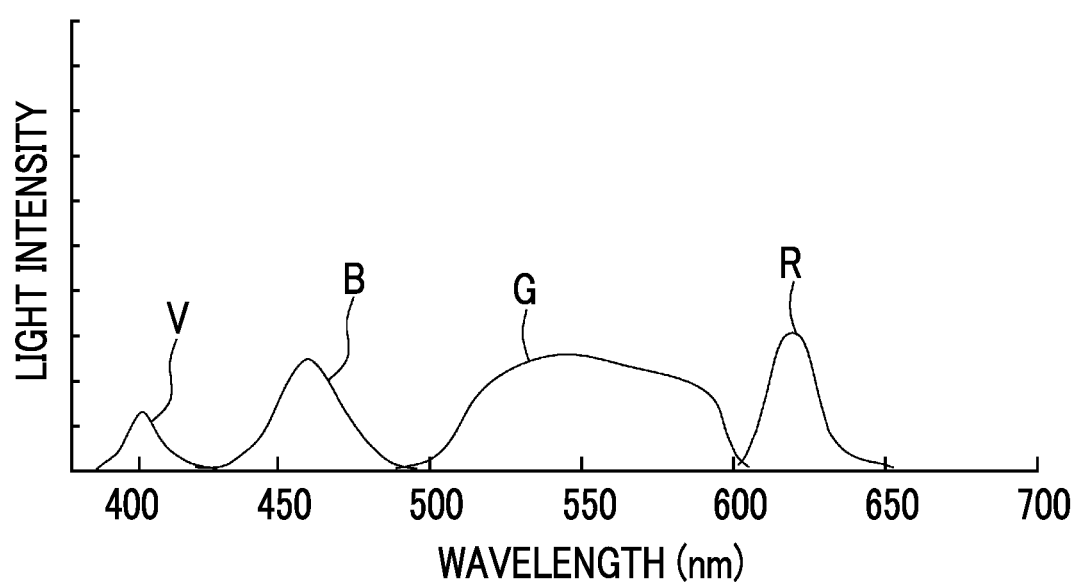
FIG. 5 is a graph showing spectra of violet light V, blue light B, green light G, and red light R.

As shown in FIG. 5, the V-LED 20a generates violet light V having a central wavelength of 410±10 nm and a wavelength range of 380 to 420 nm. The B-LED 20b generates blue light B having a central wavelength of 450±10 nm and a wavelength range of 420 to 500 nm. The G-LED 20c generates green light G having a wavelength range of 480 to 600 nm. The R-LED 20d generates red light R having a central wavelength of 620 to 630 nm and a wavelength range of 600 to 650 nm. In the present specification, the term "to" between numerical values indicates a range including the numerical values before and after, and for example, "420 to 500 nm" means "420 nm or more and 500 nm or less".

The light source processor 21 controls the V-LED 20a, the B-LED 20b, the G-LED 20c, and the R-LED 20d. The light source processor 21 controls the respective LEDs 20a to 20d such that a normal light beam of which the combination of light intensity ratios between violet light V, blue light B, green light G, and red light R is Vc:Bc:Gc:Rc is emitted in the normal observation mode.

Figure 6:
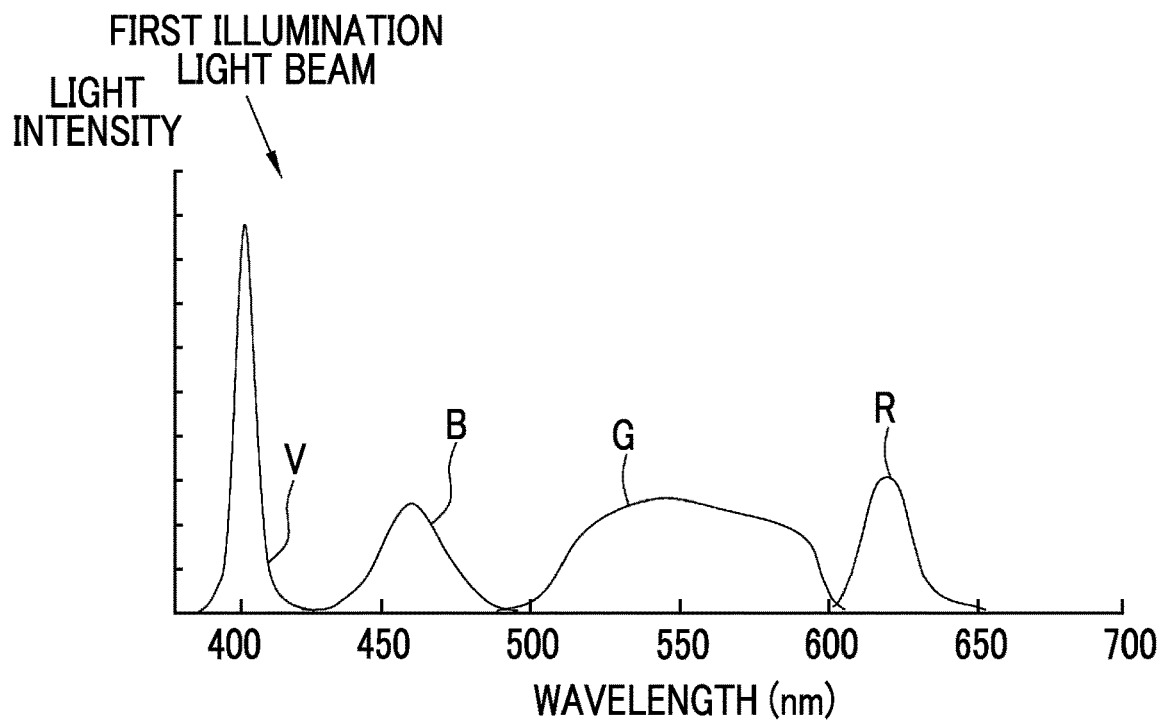
FIG. 6 is a graph showing a spectrum of a first illumination light beam.

The light source processor 21 controls the respective LEDs 20a to 20d such that a first illumination light beam of which the combination of the light intensity ratios between violet light V, blue light B, green light G, and red light R is Vs1:Bs1:Gs1:Rs1 is emitted in the first special observation mode. It is preferable that the first illumination light beam enhances superficial blood vessels. For this purpose, it is preferable that the light intensity of violet light V of the first illumination light beam is set to be higher than the light intensity of green light G. For example, as shown in FIG. 6, a ratio of the light intensity Vs1 of violet light V to the light intensity Gs1 of green light G is set to "4:1".

In the present specification, the combination of the light intensity ratios includes a case where the ratio of at least one semiconductor light source is zero. Therefore, the combination of the light intensity ratios includes a case where any one or two or more of the semiconductor light sources are not turned on. For example, a case where only one semiconductor light source is turned on and the other three semiconductor light sources are not turned on as in a case where the combination of the light intensity ratios between violet light V, blue light B, green light G, and red light R is 1:0:0:0 is also regarded that the light source unit 20 has light intensity ratios, and is one of the combinations of the light intensity ratios.

Figure 7:
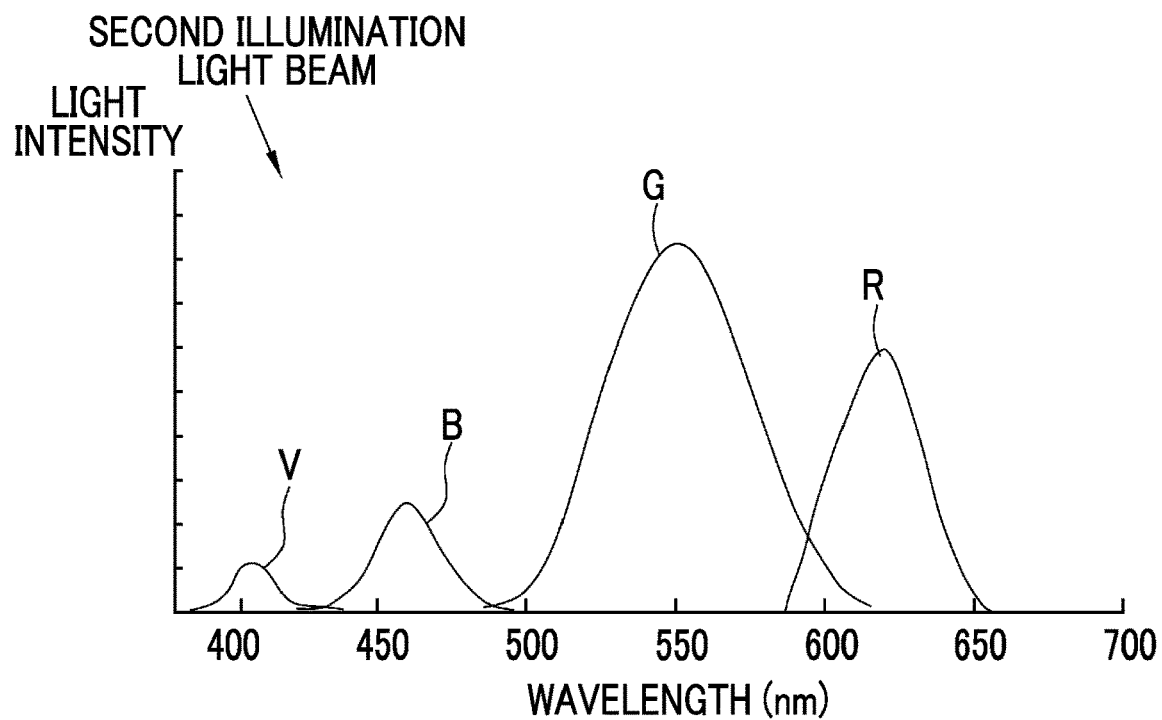
FIG. 7 is a graph showing a spectrum of a second illumination light beam.

Further, the light source processor 21 controls the respective LEDs 20a to 20d such that a second illumination light beam of which the combination of the light intensity ratios between violet light V, blue light B, green light G, and red light R is Vs2:Bs2:Gs2:Rs2 is emitted in the second special observation mode. It is preferable that the second illumination light beam enhances deep blood vessels. For this purpose, it is preferable that the light intensity of green light G of the second illumination light beam is set to be higher than the light intensity of the violet light V and the blue light B. For example, as shown in FIG. 7, a ratio of the light intensity Vs2 of violet light V to the light intensity Bs2 of blue light B is set to "1:3".

In the normal observation mode, the first special observation mode, or the second special observation mode, the combinations of the light intensity ratios between violet light V, blue light B, green light G, and red light R, that is, the types of the illumination light beam, are different from each other. The light source processor 21 performs control to switch the first illumination light beam to an illumination light beam of which a combination of the light intensity ratios is different from the first illumination light beam, for example, the second illumination light beam, to emit the second illumination light beam for a period of at least one frame, during a first period in which a specific type of illumination light beam, for example, the first illumination light beam is emitted. The light source processor 21 performs control to switch the second illumination light beam to an illumination light beam of which a combination of the light intensity ratios is different from the second illumination light beam, for example, the first illumination light beam, to emit the first illumination light beam for a period of at least one frame, during a second period in which the second illumination light beam is emitted. In a case where the light source processor 21 switches a specific type of illumination light beam to the other type of illumination light beam to emit the other type of illumination light beam, during a period in which the specific type of illumination light beam is emitted, the specific type of illumination light beam may be switched to the other type of illumination light beam at any time in point within the period of at least one frame, but control may be performed such that the other type of illumination light beam is periodically emitted in a preset cycle. Since the period during which the specific type of illumination light beam is emitted is a period during which the specific type of illumination light beam is continuously emitted, the specific type of illumination light beam may be emitted again, after the specific type of illumination light beam is switched to the other type of illumination light beam and the other type of illumination light beam is emitted during the period in which the specific type of illumination light beam is emitted.

"Frame" means a unit that is used to control an image pickup sensor 45 (see FIG. 3) that picks up the image of the observation target. For example, "one frame" means a period including at least an exposure period in which the image pickup sensor 45 is exposed to light beams emitted from the observation target and a read-out period in which image signals are read out. In the present embodiment, the first period or the second period is defined so as to correspond to the "frame" that is a unit of image pickup.

Figure 8:
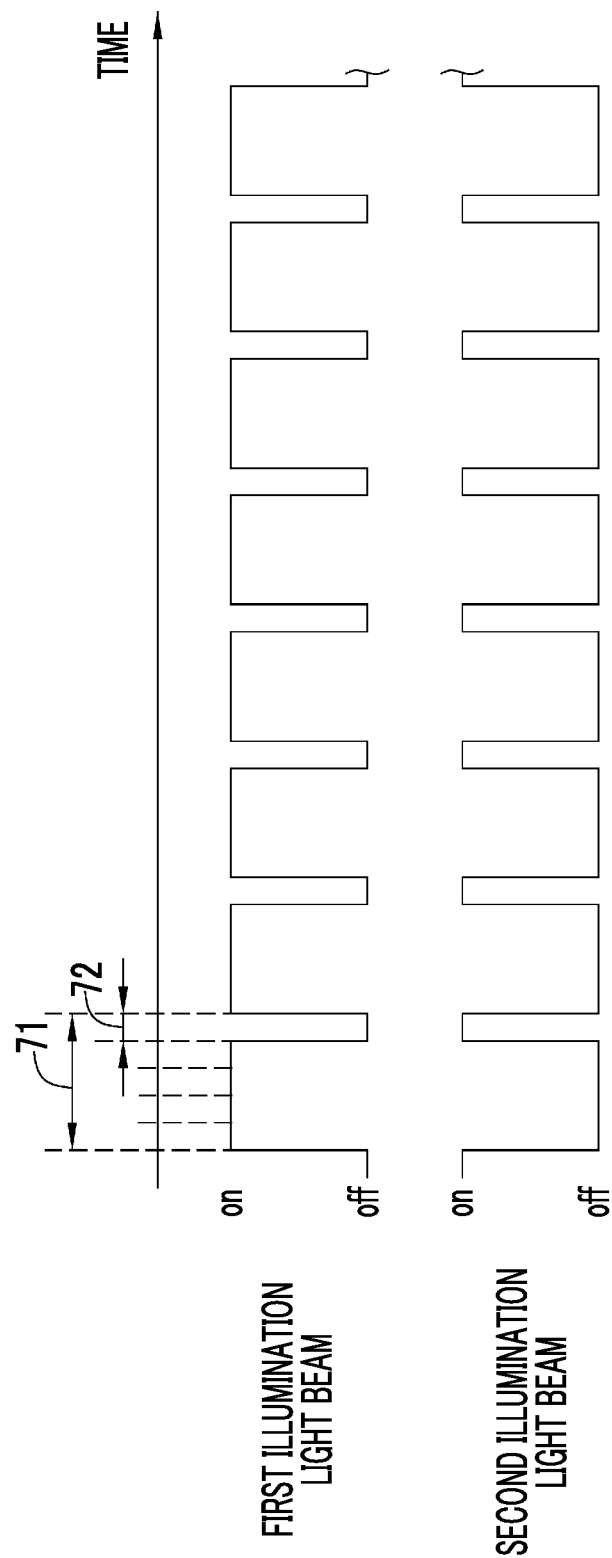
FIG. 8 is a diagram illustrating an illumination light beam in a first special observation mode.
Figure 9:
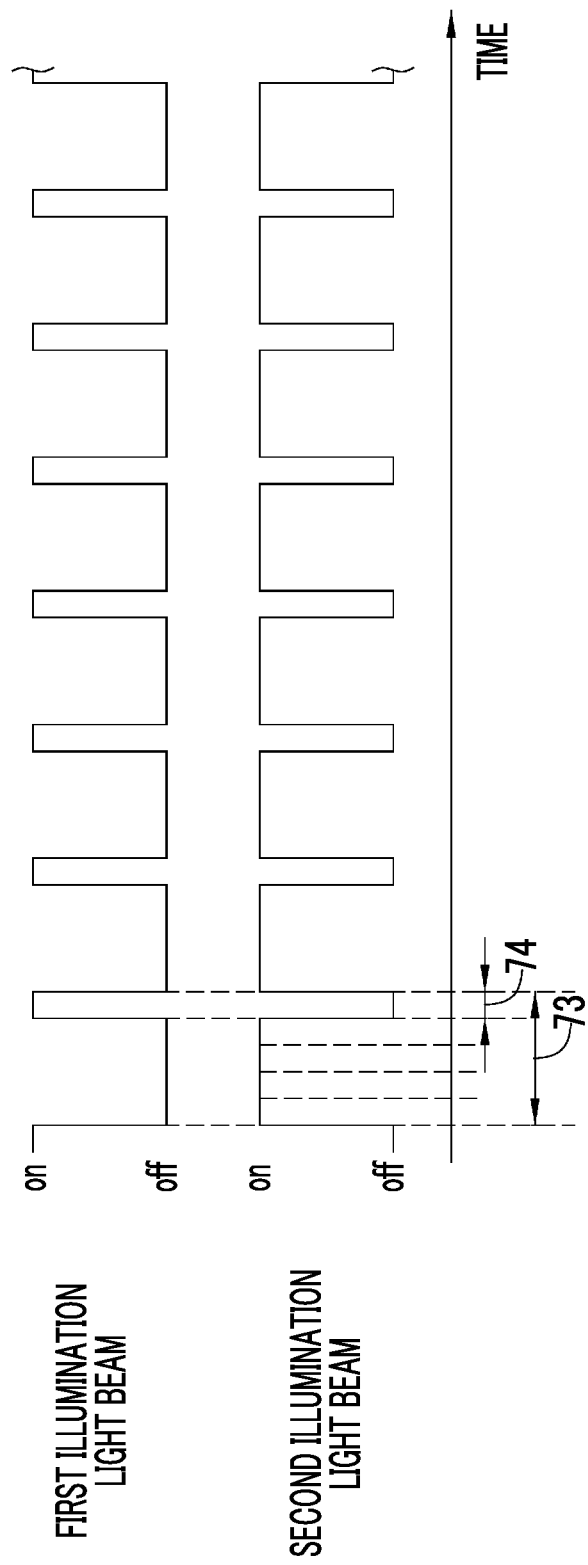
FIG. 9 is a diagram illustrating an illumination light beam in a second special observation mode.

The above-described light emission control in the first period or the second period performed by the light source processor 21 in the special observation mode will be described in detail. As described in FIG. 8, the first illumination light beam is switched to the second illumination light beam and the second illumination light beam is emitted in a cycle of a second illumination light emission period 72 for one frame with respect to a first illumination light emission period 71 for four frames, during the first period in which the first illumination light beam is continuously emitted, and the cycle is repeated. Alternatively, as shown in FIG. 9, the second illumination light beam is switched to the first illumination light beam and the first illumination light beam is emitted in a cycle of a first illumination light emission period 74 for one frame with respect to a second illumination light emission period 73 for five frames, during the second period in which the second illumination light beam is continuously emitted, and the cycle is repeated. In the figure, in order to avoid complicating the figure, only a part thereof is given a reference numeral.

The light source processor 21 alternately repeats specific types of illumination light beams, for example, the first period in which the first illumination light beam is continuously emitted and the second period in which the second illumination light beam is emitted, in a case where the multi-observation mode is set. In the multi-observation mode, for example, the light source processor 21 performs control to switch the first illumination light beam to the second illumination light beam to emit the second illumination light beam for a period of at least one frame, during the first period, and performs control to switch the second illumination light beam to the first illumination light beam to emit the first illumination light beam for a period of at least one frame, during the second period.

Figure 10:
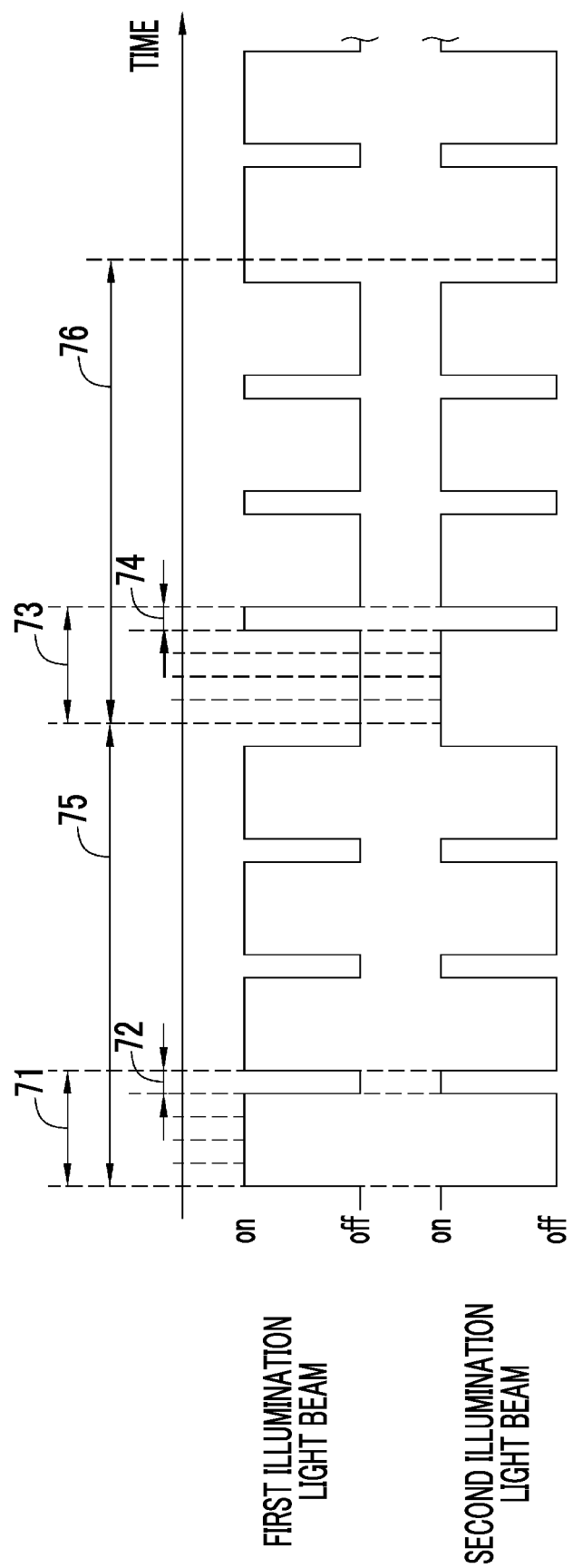
FIG. 10 is a diagram illustrating an illumination light beam in a multi-observation mode.

The light emission control in the multi-observation mode performed by the light source processor 21 will be described in detail. As shown in FIG. 10, the first illumination light beam is switched to the second illumination light beam and the second illumination light beam is emitted in a cycle of the second illumination light emission period 72 for one frame with respect to the first illumination light emission period 71 for four frames, in a first period 75 in which the first illumination light beam is continuously emitted, and the cycle is repeated during the first period 75. After that, the second illumination light beam is switched to the first illumination light beam and the first illumination light beam is emitted in a cycle of the first illumination light emission period 74 for one frame with respect to the second illumination light emission period 73 for five frames, in a second period 76 in which the second illumination light beam is continuously emitted, and the cycle is repeated during the second period 76. After that, the period returns to the first period 75 in which the first illumination light beam is continuously emitted, and the first period 75 and the second period 76 are alternately repeated. In the present embodiment, the first period 75 and the second period 76 each correspond to 20 frames.

Figure 11:
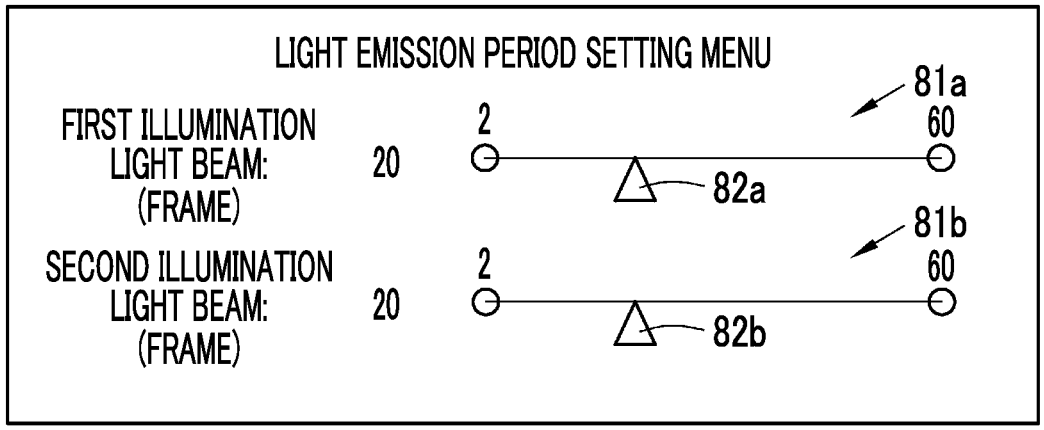
FIG. 11 is a diagram illustrating a light emission period setting menu.

The first period that is the light emission period of the first illumination light beam and the second period that is the light emission period of the second illumination light beam can be appropriately changed by the light emission period setting unit 22 that is connected to the light source processor 21. In a case where an operation for changing the light emission period is received by the operation of the keyboard 19, the light emission period setting unit 22 displays a light emission period setting menu shown in FIG. 11 on the display 18. The first period can be changed, for example, between 2 frames and 60 frames, and the respective light emission periods are assigned on a slide bar 81a. The second period can be also changed, for example, between 2 frames and 60 frames, and the respective light emission periods are assigned on a slide bar 81b.

In a case of changing the first period, a slider 82a is positioned, through the operation of the keyboard 19, at a position on the slide bar 81a indicating a light emission period to be changed, whereby the first period is changed. Also in the second period, a slider 82b is positioned, through the operation of the keyboard 19, at a position on the slide bar 81b indicating a light emission period to be changed, whereby the second period is changed. The slide bar 81b is also assigned the light emission periods, for example, from 2 frames to 60 frames. In the present embodiment, in the multi-observation mode, the first period is assigned the light emission period for 20 frames through the slide bar 81a, and the second period is assigned the light emission period for 20 frames through the slide bar 81*b*.

A light beam emitted from each of the LEDs 20*a* to 20*d* is incident on a light guide 41 through an optical path coupling unit (not shown) that is composed of a mirror, a lens, or the like. The light guide 41 is incorporated in the endoscope 12 and a universal cord (a cord that connects the endoscope 12 to the light source device 14 and the processor device 16). The light guide 41 propagates the light beam from the optical path coupling unit to the distal end portion 12*d* of the endoscope 12.

The distal end portion 12*d* of the endoscope 12 is provided with an illumination optical system 30*a* and an image pickup optical system 30*b*. The illumination optical system 30*a* has an illumination lens 42, and the observation target is irradiated with the illumination light beam propagated by the light guide 41, through the illumination lens 42. The image pickup optical system 30*b* has an objective lens 43, a zoom lens 44, and an image pickup sensor 45. Various types of light beams, such as light reflected from the observation target, scattered light, and fluorescence, are incident on the image pickup sensor 45 through the objective lens 43 and the zoom lens 44. With this, the image of the observation target is formed on the image pickup sensor 45. The zoom lens 44 is freely moved between the telephoto end and the wide end by the operation of the zoom operation portion 12*h*, and magnifies and reduces the observation target of which the image is formed on the image pickup sensor 45.

The image pickup sensor 45 is a color image pickup sensor provided with any one of a red (R) color filter, a green (G) color filter, or a blue (B) color filter for each pixel, and picks up the image of the observation target to output image signals of respective RGB colors. A charge coupled device (CCD) image pickup sensor or a complementary metal-oxide semiconductor (CMOS) image pickup sensor can be used as the image pickup sensor 45. Alternatively, a complementary color image pickup sensor provided with color filters of complementary colors, that is, cyan (C), magenta (M), yellow (Y), and green (G), may be used instead of the image pickup sensor 45 provided with color filters of the primary colors. In a case where the complementary color image pickup sensor is used, the image signals of four colors of CMYG are output. Therefore, the same RGB image signals as those of the image pickup sensor 45 can be obtained by converting the image signals of the four colors of CMYG into the image signals of the three colors of RGB through the complementary color-primary color conversion. Alternatively, a monochrome image pickup sensor that is not provided with color filters may be used instead of the image pickup sensor 45.

The image pickup sensor 45 is driven and controlled by an image pickup processor (not shown). The control performed by the image pickup processor differs depending on the respective modes. In the normal observation mode, the image pickup processor controls the image pickup sensor 45 to pick up the image of the observation target illuminated with a normal light beam. With this, Bc image signals are output from B pixels of the image pickup sensor 45, Gc image signals are output from G pixels thereof, and Rc image signals are output from R pixels thereof. In the special observation mode or the multi-observation mode, the image pickup processor controls the image pickup sensor 45 to pick up the image of the observation target illuminated with a special light beam. With this, in the first special observation mode, Bs1 image signals are output from the B pixels of the image pickup sensor 45, Gs1 image signals are output from the G pixels thereof, and Rs1 image signals are output from the R pixels thereof. Similarly, in the second special observation mode, Bs2 image signals are output from the B pixels of the image pickup sensor 45, Gs2 image signals are output from the G pixels thereof, and Rs2 image signals are output from the R pixels thereof.

A correlated double sampling/automatic gain control (CDS/AGC) circuit 46 performs correlated double sampling (CDS) or automatic gain control (AGC) on the analog image signals obtained from the image pickup sensor 45. The image signals that have been passed through the CDS/AGC circuit 46 are converted into digital image signals by an analog/digital (A/D) converter 47. The digital image signals that have been subjected to A/D conversion are input to the processor device 16.

In the processor device 16, a program related to processing such as image storage processing is stored in the program memory (not shown). In the processor device 16, the program stored in the program memory operates through a central control unit 62 composed of the image processor, whereby functions of an image signal acquisition unit 51, a digital signal processor (DSP) 52, a noise reduction unit 53, a memory 54, a signal processing unit 55, an image storage unit 56, an image storage control unit 61, a display control unit 57, and a video signal generation unit 58 are realized. Further, the central control unit 62 receives information input from the endoscope 12 and the light source device 14, and controls each unit of the processor device 16 and controls the endoscope 12 or the light source device 14, on the basis of the received information. Further, the central control unit 62 also receives information, such as an instruction input from the keyboard 19.

The image signal acquisition unit 51 acquires the digital image signals of an endoscopic image, which are input from the endoscope 12. The image signal acquisition unit 51 acquires image signals obtained by imaging the observation target illuminated with each illumination light beam, for each frame. The acquired image signals are transmitted to the DSP 52. The DSP 52 performs various types of signal processing, such as offset processing, defect correction processing, demosaicing processing, linear matrix processing, gain correction processing, gamma conversion processing, and YC conversion processing, on the received image signals. In the offset processing, dark current components are removed from the received image signals, and an accurate zero level is set. In the defect correction processing, signals of defective pixels of the image pickup sensor 45 are corrected. The demosaicing processing (also referred to as equalization processing or demosaicing) is performed on the image signals that have been subjected to the defect correction processing, and signals of lacking color in each pixel are generated by interpolation. All the pixels are made to have signals of the respective RGB colors through the demosaicing processing.

The linear matrix processing of improving color reproducibility is performed on the image signals of each color, which have been subjected to the demosaicing processing. In the gain correction processing, the image signals of each color, which have been subjected to the demosaicing processing, are multiplied by a specific gain, whereby the signal level of each image signal is adjusted. After that, the brightness or chroma saturation of each image signal is adjusted through the gamma conversion processing. The DSP 52 performs the YC conversion processing on each image signal that has been subjected to the gamma conversion processing, and outputs brightness signals Y, color difference signals Cb, and color difference signals Cr to the noise reduction unit 53.

The noise reduction unit 53 performs noise reduction processing, which is performed through, for example, a moving average method or median filtering method, on the image signals that have been subjected to the gamma conversion processing and the like by the DSP 52. The image signals with reduced noise are stored in the memory 54.

The signal processing unit 55 acquires the noise-reduced image signals from the memory 54. Then, signal processing, such as color conversion processing, hue enhancement processing, and structure enhancement processing, is performed as necessary on the acquired image signals, and a color endoscopic image in which the observation target is imaged is generated. The color conversion processing is processing of performing color conversion through 3×3 matrix processing, gradation transformation processing, three-dimensional look-up table (LUT) processing, and the like, on the image signals. The hue enhancement processing is performed on the image signals that have been subjected to the color conversion processing. The structure enhancement processing is processing of enhancing, for example, a specific tissue or structure included in the observation target, such as blood vessels or pit patterns, and is performed on the image signals that have been subjected to the hue enhancement processing.

In the normal observation mode, the signal processing unit 55 performs image processing for a normal image on the input noise-reduced image signals for one frame. The image processing for a normal image includes color conversion processing, such as 3×3 matrix processing, gradation transformation processing, and three-dimensional LUT processing, hue enhancement processing, and structure enhancement processing, such as spatial frequency enhancement. The image signals that have been subjected to the image processing for a normal image are input to the image storage unit 56, as a normal image.

In the special observation mode, the signal processing unit 55 performs image processing for a special image on the noise-reduced image signals for one frame, which are input in the first special observation mode or the second special observation mode. The image processing for a special image includes color conversion processing, such as 3×3 matrix processing, gradation transformation processing, and three-dimensional LUT processing, hue enhancement processing, and structure enhancement processing, such as spatial frequency enhancement. The image signals that have been subjected to the image processing for a special image is input to the image storage unit 56, as the first image or the second image.

Since the endoscopic image generated by the signal processing unit 55 is a normal observation image in a case where the observation mode is the normal observation mode and is a special observation image in a case where the observation mode is the special observation mode, the contents of the color conversion processing, the hue enhancement processing, and the structure enhancement processing differ depending on the observation modes. In the normal observation mode, the signal processing unit 55 generates the normal observation image by performing the above various types of signal processing of making the observation target have natural color tones. In the special observation mode, the signal processing unit 55 generates the special observation image including the first image and the second image by performing the above various types of signal processing of enhancing, for example, the blood vessels of the observation target.

The semiconductor light sources include a first semiconductor light source that emits violet light V (first narrow-band light beam) having a wavelength band of which the central wavelength is 410±10 nm and the wavelength range is 380 to 420 nm, and a second semiconductor light source that emits blue light B (second narrow-band light beam) having a wavelength band of which the central wavelength is 450±10 nm and the wavelength range is 420 to 500 nm. Therefore, in the special observation image generated by the signal processing unit 55, blood vessels (so-called superficial blood vessels) or blood located at a relatively shallow position in the observation target with a surface of the mucous membrane as a reference has magenta-based color (for example, brown color) in the first image, and blood vessels (so-called medium-depth blood vessels) located at a relatively deep position in the observation target with the surface of the mucous membrane as a reference have cyan-based color (for example, green color) in the second image. Therefore, the blood vessels or hemorrhage (blood) of the observation target is enhanced by a difference in color with respect to the mucous membrane represented by pink-based color.

Figure 12:
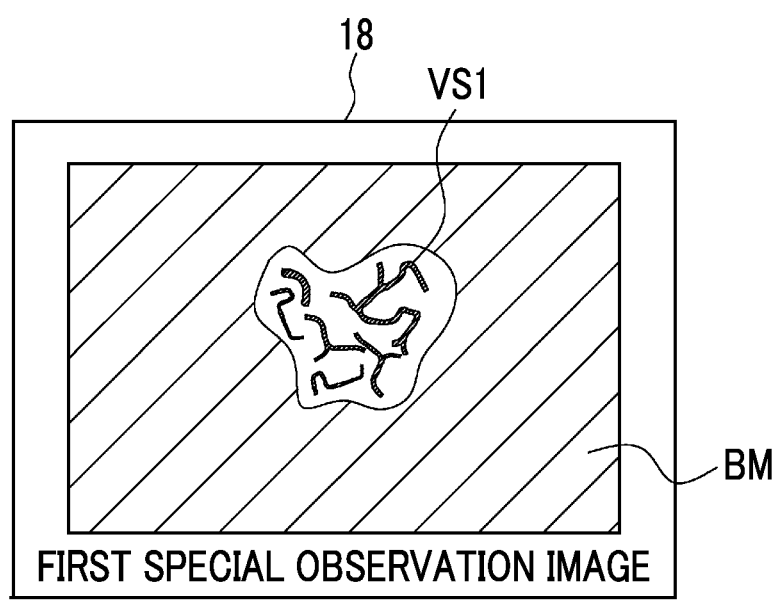
FIG. 12 is an image diagram showing a first special observation image.
Figure 13:
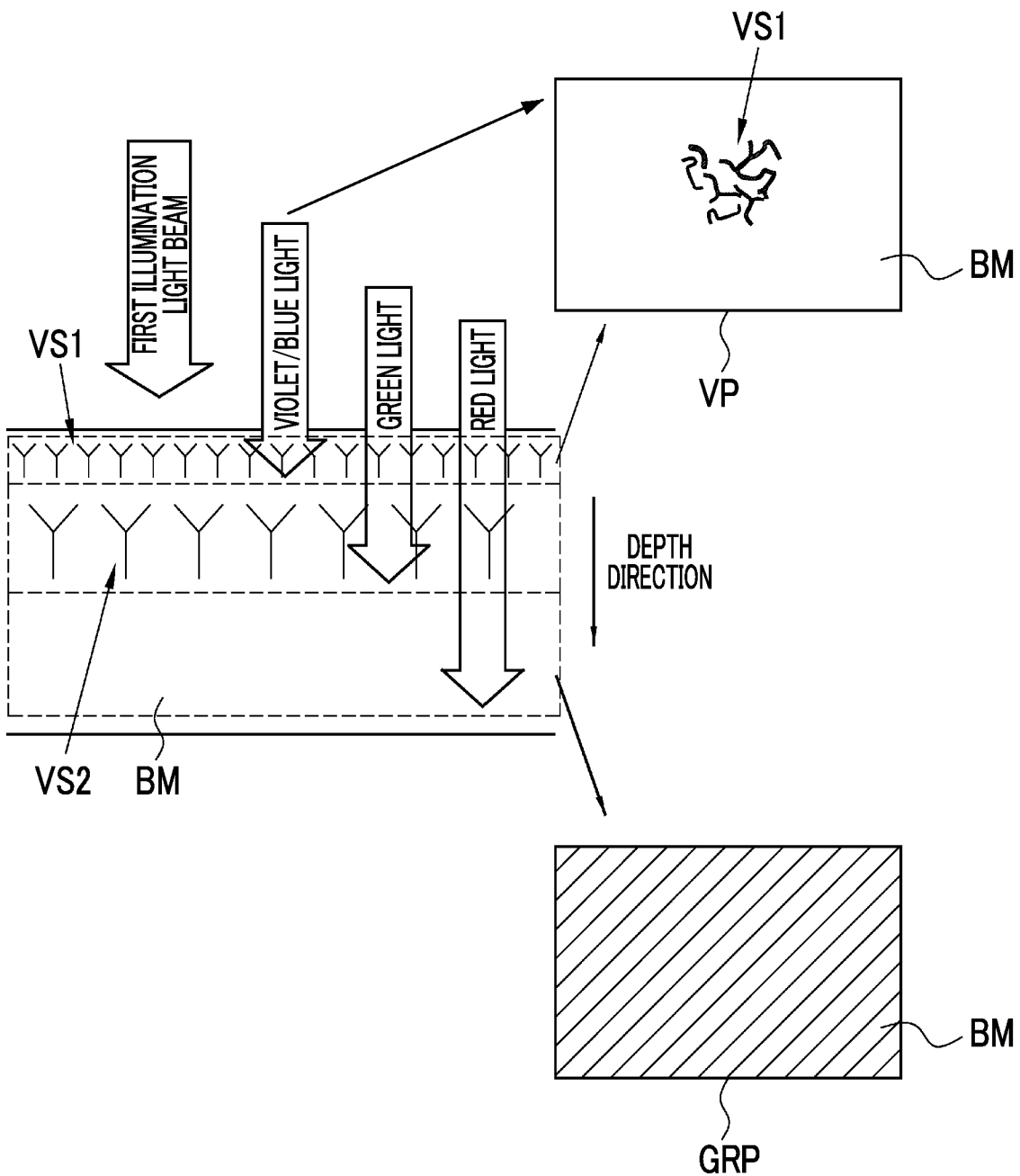
FIG. 13 is a diagram illustrating a violet and blue light image and a green and red light image that are obtained in a case where an observation target is illuminated with the first illumination light beam.

As shown in FIG. 12, an image in which a background mucous membrane BM and superficial blood vessels VS1, out of the observation targets, are shown is displayed in the first image. The first image is obtained on the basis of the first illumination light beam including violet light, blue light, green light, and red light. As shown in FIG. 13, in a case where the observation target is illuminated with the first illumination light beam, violet light V and blue light B of the first illumination light beam reach a surface layer where the superficial blood vessels VS1 are distributed. Accordingly, a violet light image VP obtained on the basis of the reflected light of violet light V and blue light B includes an image of the superficial blood vessels VS1. Here, since the light intensity of violet light V is higher than the light intensity of blue light B, the image obtained on the basis of the reflected light of violet light V and blue light B is referred to as a violet light image VP. Further, green light G of the first illumination light beam reaches deep blood vessels VS2 (blood vessels located at positions deeper than the superficial blood vessels VS1) and red light R of the first illumination light beam reaches-reach the background mucous membrane BM that is distributed at a position deeper than the superficial blood vessels VS1 and the deep blood vessels VS2. Accordingly, a green and red light image GRP obtained on the basis of the reflected light of green light G and red light R includes an image of the deep blood vessels VS2 and an image of the background mucous membrane BM. As described above, since the first image is an image in which the violet light image VP and the green and red light image GRP are combined with each other, the images of the background mucous membrane BM, the superficial blood vessels VS1 and the deep blood vessels VS2 are displayed.

Figure 14:
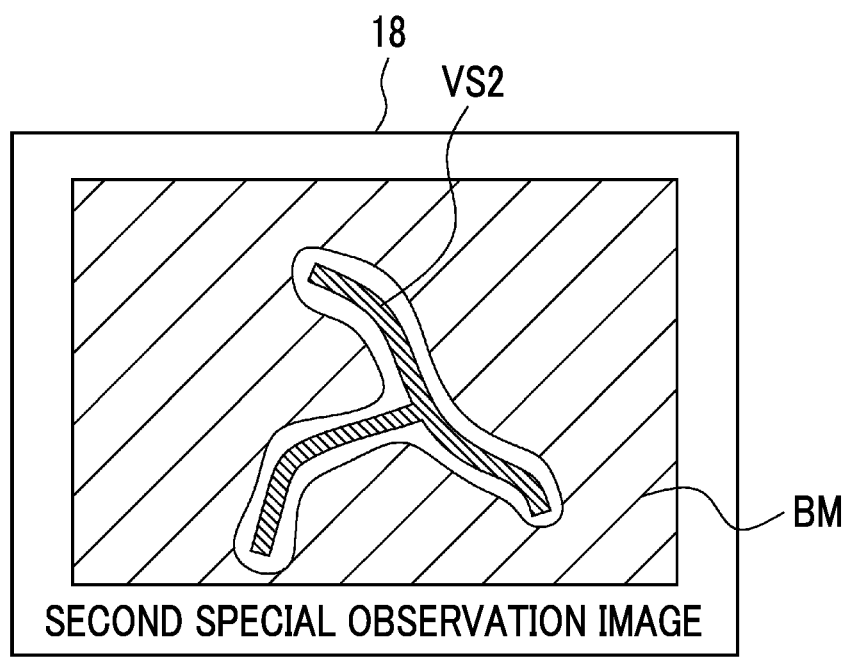
FIG. 14 is an image diagram showing a second special observation image.
Figure 15:
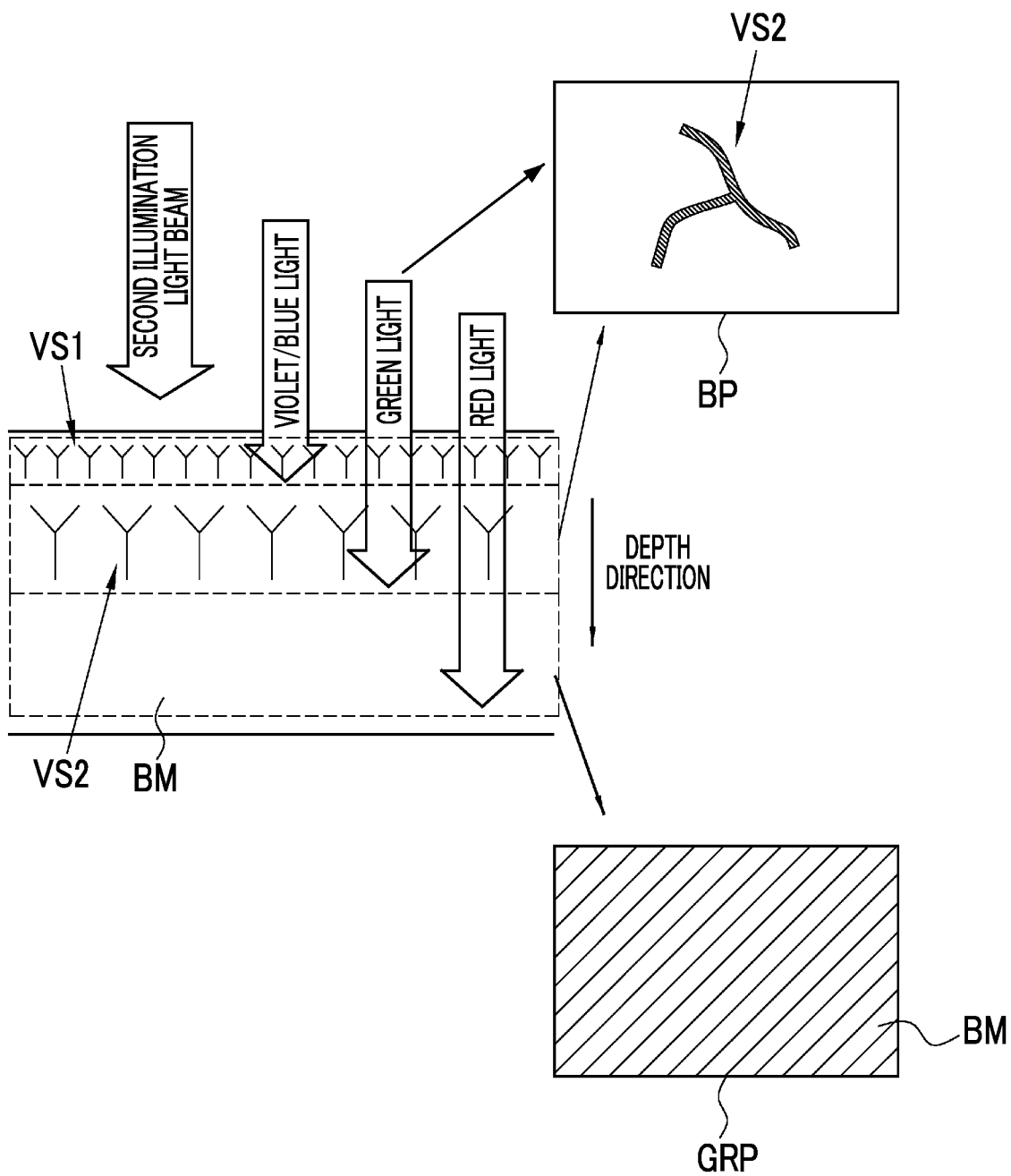
FIG. 15 is a diagram illustrating a violet and blue light image and a green and red light image that are obtained in a case where an observation target is illuminated with the second illumination light beam.

As shown in FIG. 14, an image in which the background mucous membrane BM and the deep blood vessels VS2, out of the observation targets, are shown is displayed in the second image. The second image is obtained on the basis of the second illumination light beam including violet light, blue light, green light, and red light. As shown in FIG. 15, in a case where the observation target is illuminated with the second illumination light beam, violet light V and blue light B of the second illumination light beam reach a surface layer where the superficial blood vessels VS1 are distributed. Accordingly, a blue light image BP obtained on the basis of the reflected light of violet light V and blue light B includes an image of the superficial blood vessels VS1. Here, since the light intensity of blue light B is higher than the light intensity of violet light V, the image obtained on the basis of the reflected light of violet light V and blue light B is referred to as a blue light image BP. Further, green light G of the second illumination light beam reaches the deep blood vessels VS2 and red light R of the second illumination light beam reaches the background mucous membrane BM that is distributed at a position deeper than the superficial blood vessels VS1 and the deep blood vessels VS2. Accordingly, a green and red light image GRP obtained on the basis of the reflected light of green light G and red light R includes an image of the deep blood vessels VS2 and an image of the background mucous membrane BM. As described above, since the second image is an image in which the blue light image BP and the green and red light image GRP are combined with each other, the images of the background mucous membrane BM, the superficial blood vessels VS1 and the deep blood vessels VS2 are displayed.

The image storage unit 56 performs image storage processing. The image storage processing is processing of storing an image, for example, processing of storing the first image and the second image. The image storage control unit 61 controls the image storage processing. Specifically, the image storage control unit 61 performs control to select at least one first image and at least one second image that satisfy a preset selection condition from a plurality of types of images acquired in a predetermined period prior to a time of the processing start operation, for example, from a plurality of the first images and a plurality of the second images, to store the at least one first image and the at least one second image in the image storage unit 56, in a case where the processing start operation for starting the image storage processing is performed.

The processing start operation is, for example, a still image acquisition instruction (freeze instruction or release instruction) operation through the still image acquisition instruction portion 12f. In a case where the still image acquisition instruction is input by the operation of the still image acquisition instruction portion 12f, the processing start operation is performed and the image storage processing is started. The image storage unit 56 stores endoscopic images such as the first image and the second image selected by the preset selection condition in the image storage unit 56 or a storage (not shown), under the control performed by the image storage control unit 61. The storage is an external storage device connected to the processor device 16 through a local area network (LAN) or the like, and is, for example, a file server of a system for filing an endoscopic image, such as a picture archiving and communication system (PACS), or a network attached storage (NAS).

Figure 16:
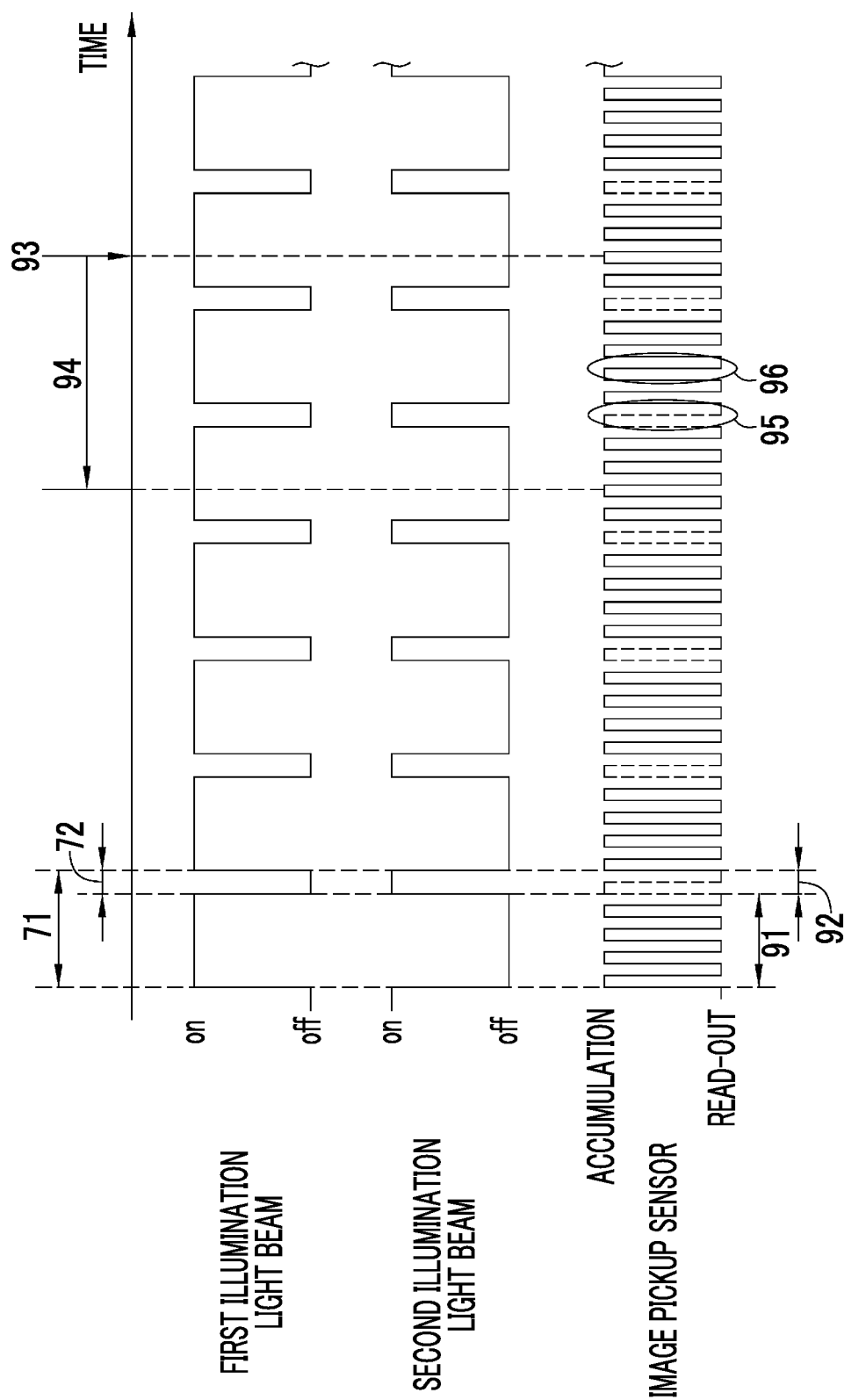
FIG. 16 is a diagram illustrating an example of storage of a still image in the first special observation mode.

As shown in FIG. 16, the image storage processing performed by the image storage control unit 61 is specifically performed as follows. In the first special observation mode, as the illumination light beam, the first illumination light beam is switched to the second illumination light beam and the second illumination light beam is emitted in a cycle of the second illumination light emission period 72 for one frame with respect to the first illumination light emission period 71 for four frames, during the first period in which the first illumination light beam is continuously emitted, and the cycle is repeated. The image pickup sensor 45 acquires image signals by performing charge accumulation and read-out for each frame. In FIG. 16, first image signal acquisition performed by the image pickup sensor 45 is shown by a solid line, and second image signal acquisition is shown by a broken line. Further, since the figure is schematically shown, for example, the time for accumulation and read-out is not always the same. As described above, the image signal acquisition unit 51 acquires the plurality of first images obtained by imaging the observation target illuminated with the first illumination light beam, in a period 91, and acquires the plurality of second images obtained by imaging the observation target illuminated with the second illumination light beam, in a period 92.

In a case where a still image acquisition instruction 93 is given, the image storage control unit 61 performs control to select at least one first image and at least one second image that satisfy the selection condition from the plurality of first images and the plurality of second images acquired in a preset predetermined period 94, to store the at least one first image and the at least one second image in the image storage unit 56. Although the selection condition can be set in advance, the selection condition is conditioned on storing the first image and the second image to be stored, in a state suitable for comparison or superimposition. For example, the image storage control unit 61 preferably sets the selection condition such that a first image and a second image having the least blur, out of the plurality of acquired first images and the plurality of acquired second images, are selected.

As a method of selecting the first image and the second image having the least blur in the first images or the second images, a known method can be used. For example, it is possible to select an image with the smallest amount of blur by calculating the amount of blur in each image. A method based on image analysis, a method based on the image pickup sensor 45, or the like is mainly used as a method of calculating the amount of blur, and there is a method of estimating a point spread function (PSF) for each of a plurality of regions in an image and of estimating the direction and magnitude of blur from the point spread function with high accuracy, as the method based on image analysis (see JP5499050B, corresponding to U.S. Pat. No. 8,723,965B2). In addition, there is a method of detecting a movement vector from image signals and of detecting the amount of blur of an image on the basis of the movement vector (see JP1991-16470A (JP-H03-16470A)). Further, a method of calculating a contrast and of detecting an image having a large contrast as an image having a small amount of blur is also preferably used.

In FIG. 16, a first image 96 and a second image 95 having the least blur, out of the plurality of first images and the plurality of second images acquired in the predetermined period 94 from the still image acquisition instruction 93, are selected. The first image 96 and the second image 95 selected by the image storage control unit 61 are stored in the image storage unit 56 by the image storage control unit 61. The image storage unit 56 uses the image signals sent from the signal processing unit 55 to perform image storage processing, and also sends the image signals to the display control unit 57 for display.

The image acquired by the image signal acquisition unit 51 or the image stored by the image storage unit 56 has a time acquired as accessory information on the image, but it is preferable that the image storage unit 56 stores the first image and the second image after adding information regarding the corresponding illumination light beams. In this case, it is preferable to have information on the illumination light beam or the observation mode, as the accessory information. Further, the file name of the image may be given, for example, identification information or an identifier associated with the illumination light beam or the observation mode, such as a tag. According to the above, it is possible to easily recognize whether the acquired or stored image is the first image or the second image.

The display control unit 57 performs control to display the image on the display 18, which is a display means. For example, the display control unit 57 performs control to continuously display the normal image as a moving image on the display 18 in the normal observation mode, to continuously display the first image or the second image as a moving image on the display 18 in the special observation mode, and to automatically switch any one of the first image or the second image to continuously display the switched image as a moving image on the display 18 in the multi-observation mode. In a case where the still image acquisition instruction 93 is given, the display control unit 57 performs control to display the endoscopic images such as the first image and the second image selected by the selection condition as still images on the display 18.

In a case where the still images such as the first image and the second image are displayed, the display control unit 57 performs control so as to display the still images in a display method set according to the purpose. Examples of the display method include a method of displaying the still images side by side on the display 18, a method of adjusting the transparency of each image to superimpose and display the still images, or a method of switching between the still images in a short time of 1 second or less on the same region of the display 18 to display the still images like an animation.

The video signal generation unit 58 converts, for example, the normal image and the special image, which are output from the display control unit 57, the first image and the second image, which are stored in the image storage unit 56, and/or the accessory information on these images into video signals that allow full-color display on the display 18. The video signals that have been converted are input to the display 18. With this, the normal image, the special image, the accessory information, or the like is displayed on the display 18.

As described above, in the endoscope system 10, while the illumination period of the illumination light beam used for observation is lengthened, the images are acquired by, for example, switching the illumination light beam to the other illumination light beam for a moment such as one frame, during the illumination period. Therefore, it is possible to easily acquire a plurality of types of images corresponding to a plurality of types of illumination light beams. Further, the switching of the illumination light beam is a momentary period such as one frame, and one type of illumination light beam is continuously emitted except for the momentary period, so that a user does not recognize the switching of the illumination and the problem of photosensitivity is less likely to occur. Accordingly, with the endoscope system 10 having the above configuration, it is possible to store a plurality of types of still images in a state suitable for comparison or superimposition, through the single still image acquisition instruction 93.

The image storage control unit 61 preferably sets the selection condition such that a first image and a second image having the smallest positional deviation between the first image and the second image selected from the plurality of acquired first images and the plurality of acquired second images are selected. The positional deviation between the selected first and second images is small, so that it is possible to store the first image and the second image in a state suitable for comparison or superimposition.

As a method of selecting the first image and the second image having the smallest positional deviation therebetween, a known method can be used. Examples of the method based on image analysis include a method of dividing the first image and the second image and comparing and obtaining the cumulative amounts of the Gs1 image signals of the first image and the Gs2 image signals of the second image having similar signal characteristics in respective regions.

Further, the image storage control unit 61 preferably sets the selection condition such that a first image and a second image having a smallest difference in acquisition time between the first image and the second image selected from the plurality of acquired first images and the plurality of acquired second images are selected. The smaller the difference in acquisition time between the selected first and second images is, the less likely it is that the positional deviation between the first image and the second image occurs, so that it is possible to store the first image and the second image in a state suitable for comparison or superimposition.

Figure 17:
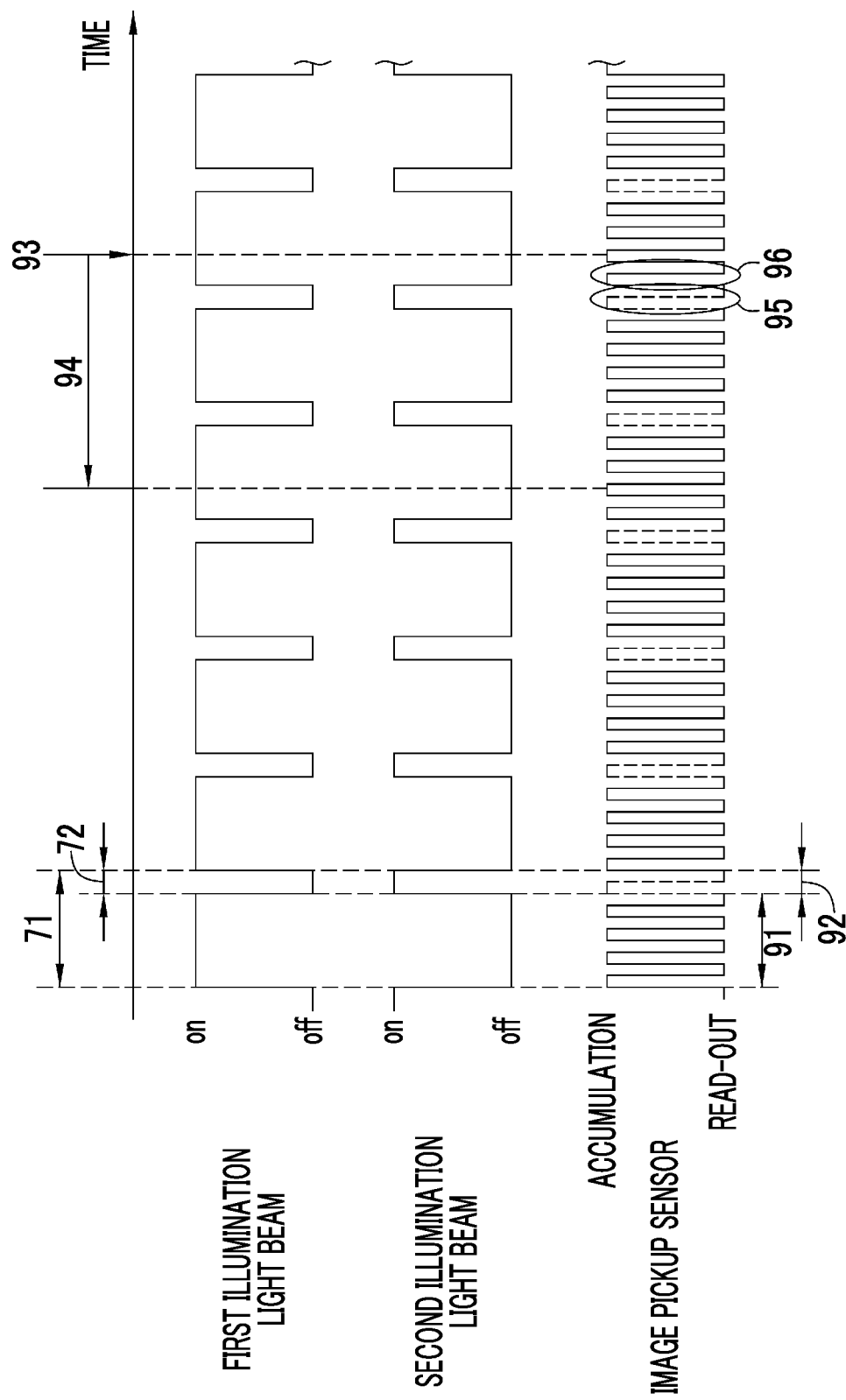
FIG. 17 is a diagram illustrating another example of the storage of the still image in the first special observation mode.

As shown in FIG. 17, in a case where the plurality of first images are acquired in the period 91 and the plurality of second images are acquired in the period 92 by the same illumination light beams, image pickup sensor 45, image signal acquisition unit 51 as in FIG. 16, the first image 96 and the second image 95 close to the time of the still image acquisition instruction 93, out of the first images and the second images having the smallest difference in acquisition time therebetween, are selected. The first image 96 and the second image 95 selected by the image storage control unit 61 are stored in the image storage unit 56 by the image storage control unit 61.

The selection condition as described above may be used alone or in combination of two or more. For example, in a case where there are a plurality of combinations of the first image and the second image having the smallest difference in acquisition time therebetween, images with less blur may be selected.

Figure 18:
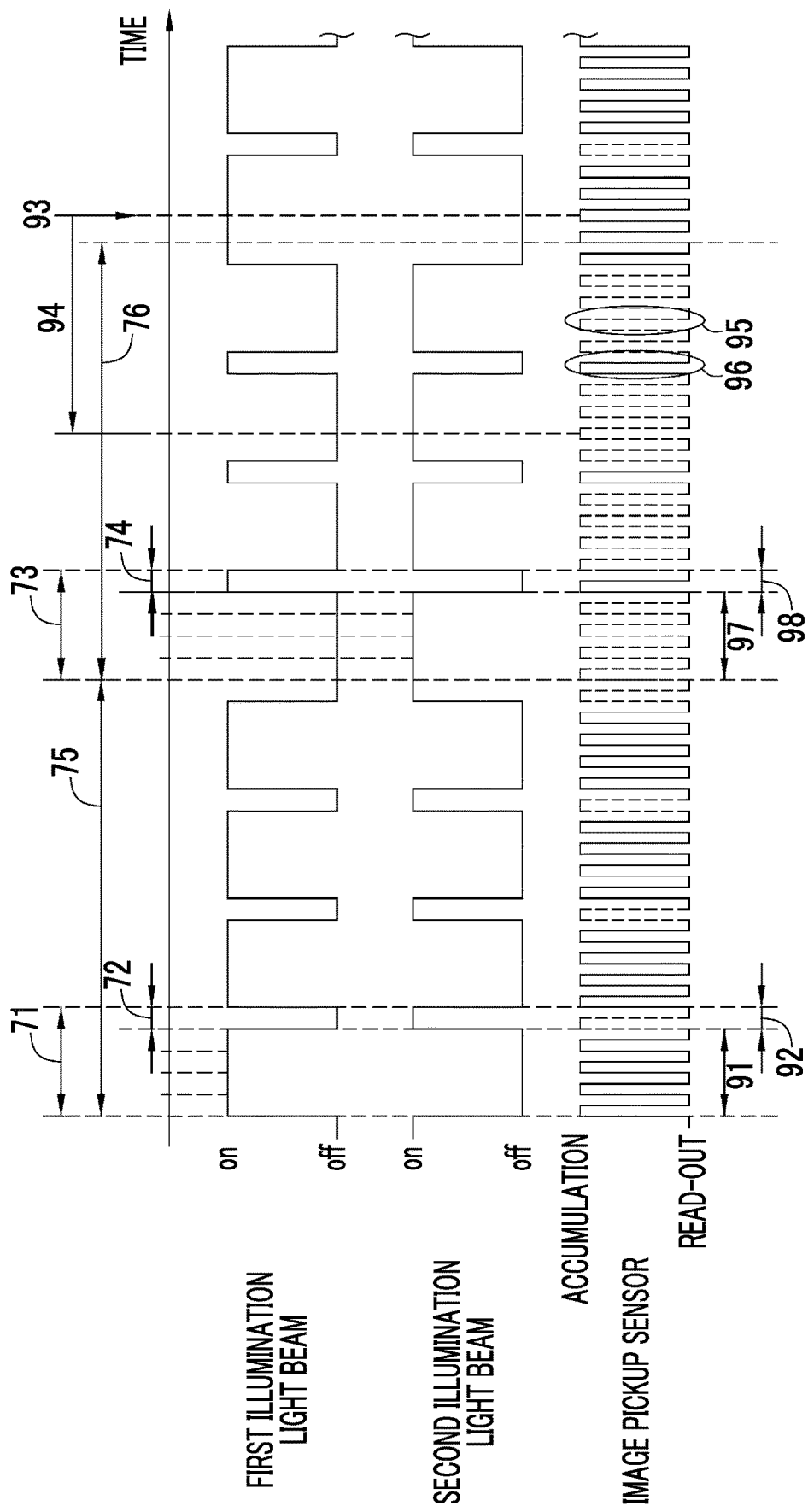
FIG. 18 is a diagram illustrating an example of storage of a still image in the multi-observation mode.

In the multi-observation mode, the image storage processing performed by the image storage control unit 61 is specifically performed as shown in FIG. 18. The illumination light beam is the illumination light beam in the multi-observation mode. In the figure, the same reference numeral indicates the same element. Therefore, in FIG. 18, the same reference numerals as those in FIG. 10 indicate the same elements. The image pickup sensor 45 acquires image signals by performing charge accumulation and read-out for each frame. In FIG. 18, the first image signal acquisition performed by the image pickup sensor 45 is shown by a solid line, and the second image signal acquisition is shown by a broken line. Therefore, the image signal acquisition unit 51 acquires the plurality of first images obtained by imaging the observation target illuminated with the first illumination light beam, in the period 91, and acquires the plurality of second images obtained by imaging the observation target illuminated with the second illumination light beam, in the period 92, and acquires the plurality of second images obtained by imaging the observation target illuminated with the second illumination light beam, in the period 97, and acquires the plurality of first images obtained by imaging the observation target illuminated with the first illumination light beam, in the period 98.

In a case where the still image acquisition instruction 93 is given, the image storage control unit 61 performs control to select at least one first image and at least one second image that satisfy the selection condition from the plurality of first images and the plurality of second images acquired in a preset predetermined period 94, to store the at least one first image and the at least one second image in the image storage unit 56. The selection condition and the like are the same as in the case of the special observation mode described above.

As described above, with the endoscope system 10, it is also possible to store a plurality of types of still images in a state suitable for comparison or superimposition, through the single still image acquisition instruction 93, in the multi-observation mode.

The display control unit 57 may perform control to continuously display the first image on the display 18 during the first period. During the first period, the first illumination light beam is switched to the second illumination light beam and the second illumination light beam is emitted for a period of at least one frame, and the image pickup sensor 45 acquires image signals for each frame, but the display 18 continuously displays the first image.

Figure 19:
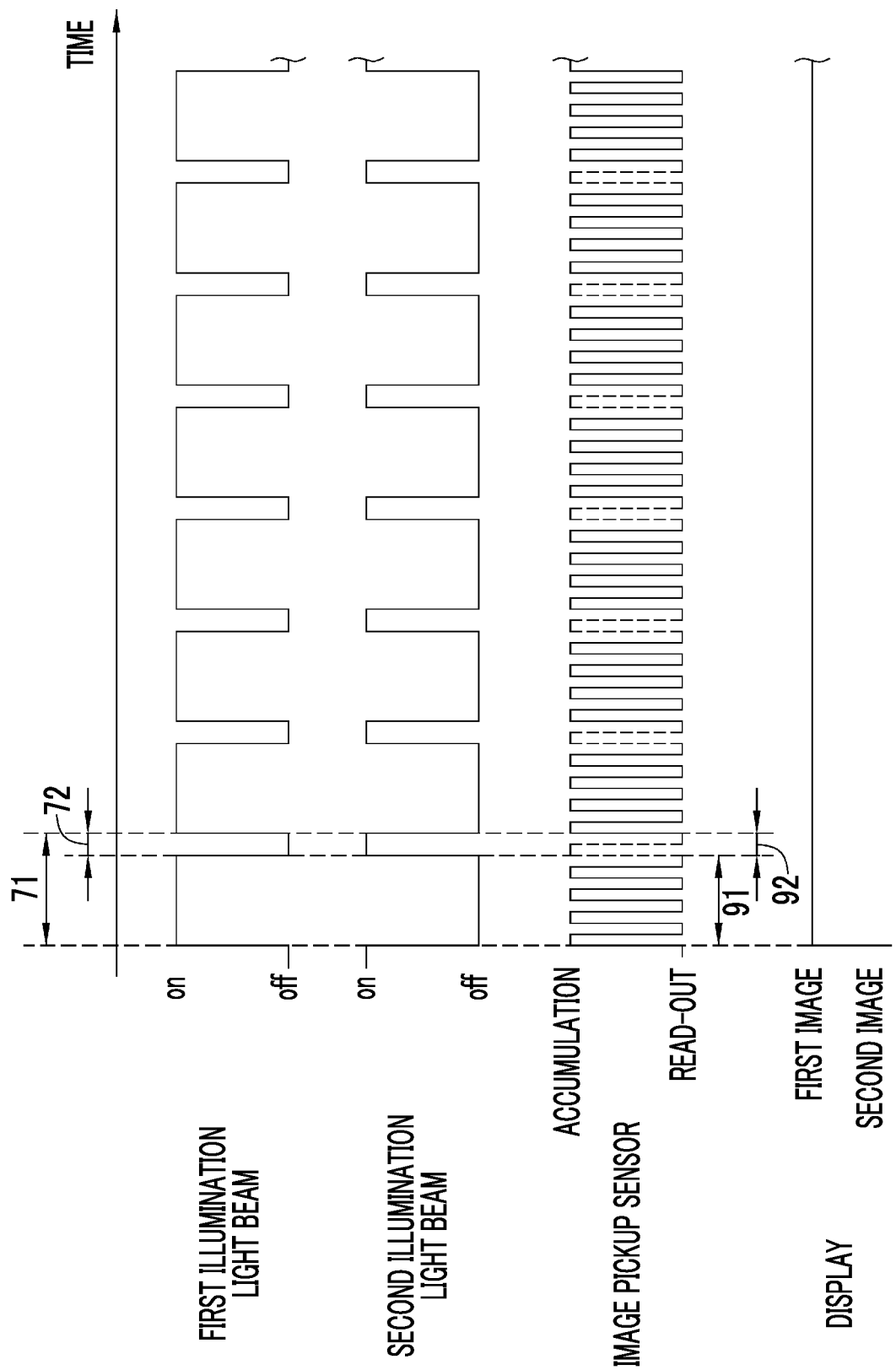
FIG. 19 is a diagram illustrating an image displayed on a display in the first special observation mode.

As shown in FIG. 19, in the first special observation mode, the image signal acquisition unit 51 acquires the plurality of first images obtained by imaging the observation target illuminated with the first illumination light beam, in a period 91, and acquires the plurality of second images obtained by imaging the observation target illuminated with the second illumination light beam, in a period 92. The display control unit 57 performs control to display the acquired first image on the display 18, and performs control not to display the acquired second image on the display 18 in the present embodiment. In this case, the display period of the first image immediately before the acquisition of the second image may be extended as it is, during the period in which the second image is acquired. Similarly, in the second special observation mode, the second image is continuously displayed.

Figure 20:
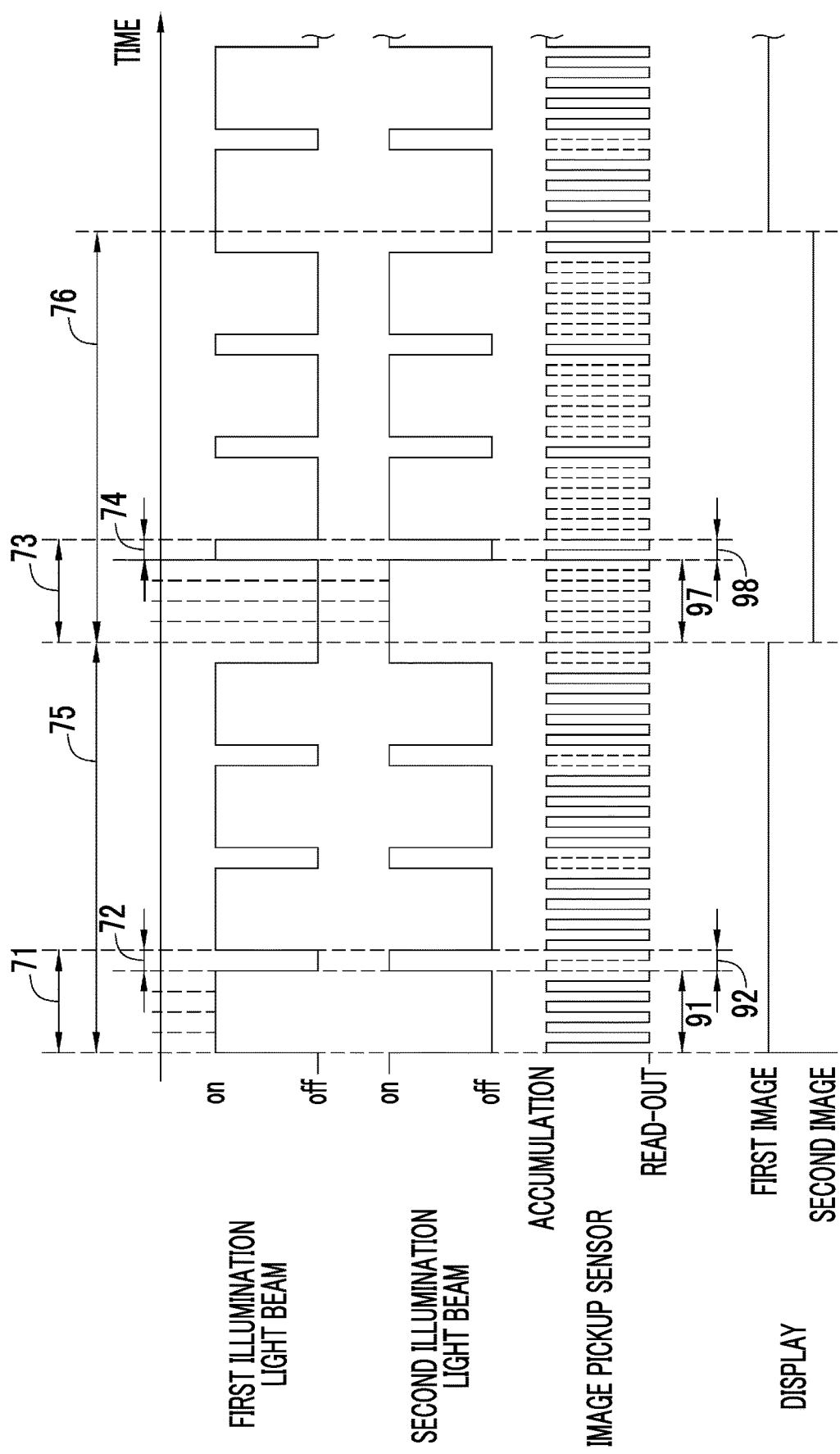
FIG. 20 is a diagram illustrating an image displayed on the display in the multi-observation mode.

In the multi-observation mode, as shown in FIG. 20, the display control unit 57 continuously displays the first image on the display 18 in the first period 75, and continuously displays the second image on the display 18 in the second period 76.

As described above, the display control unit 57 performs control to continuously display the first image on the display 18 during the first period, so that it is possible to display the endoscopic images on the display 18 without flicker or the like while acquiring image signals having a mode different from the mode being observed. Accordingly, the user can perform observation and the like more stably.

Figure 21:
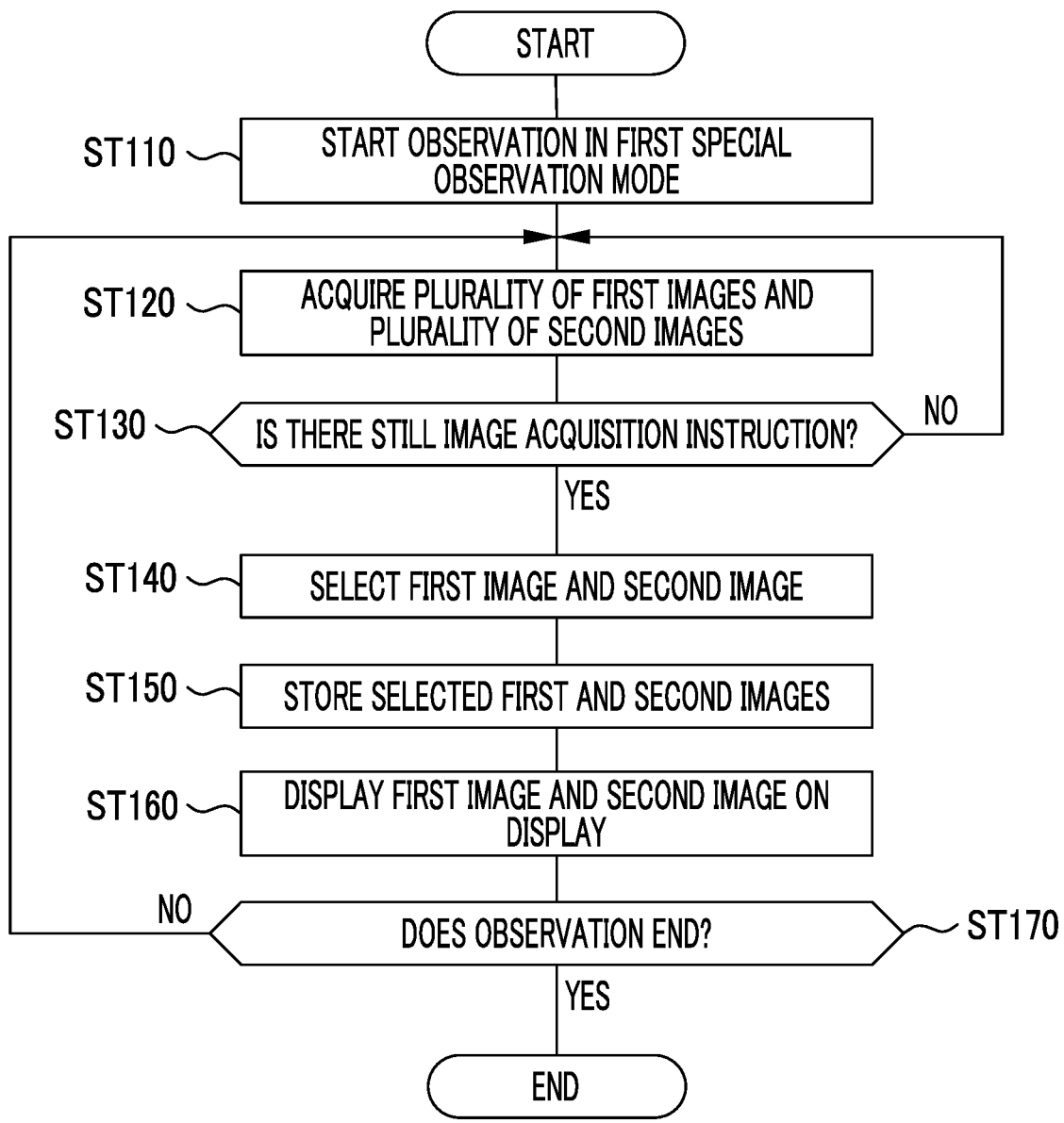
FIG. 21 is a flowchart showing a series of flows of the storage of the still image in the first special observation mode.

Next, a series of flows of still image storage will be described with reference to the flowchart shown in FIG. 21. In the case of the first special observation mode, observation is performed in the first special observation mode (step ST110). During the observation, the image signal acquisition unit 51 acquires the first image and the second image (step ST120). In this case, as the endoscopic image displayed on the display 18, the first image may be continuously displayed, or the display may be switched between the first image and the second image in accordance with the acquisition of the image.

In a case where there is the still image acquisition instruction (YES in step ST130), at least one first image and at least one second image that satisfy the preset selection condition are selected (step ST140) from the plurality of first images and the plurality of second images, which are acquired by the image signal acquisition unit 51 in the predetermined period prior to the time of the still image acquisition instruction, because the still image acquisition instruction corresponds to the processing start operation of the image storage processing. In a case where there is no still image acquisition instruction (NO in step ST130), the observation and the acquisition of the first image and the second image are continued. The selected first and second images are stored by the image storage unit 56 (step ST150). The display control unit 57 displays the stored first and second images on the display 18 (step ST160). The display format is a preset format, and for example, two images are superimposed and displayed on the display 18. In a case where the observation is completed (YES in step ST170), a series of flows ends. In a case where the observation is continued (NO in step ST170), the process returns to the observation in the first special observation mode.

In the above embodiment, the present invention is applied to the endoscope system that performs processing on the endoscopic image, but the present invention can also be applied to a medical image processing system that processes medical images other than the endoscopic image, in a case where the still image is stored.

In the above embodiment, the hardware structures of the light source processor 21, the image pickup processor, and the processing units that execute various types of processing, such as the central control unit 62, the image signal acquisition unit 51, the DSP 52, the noise reduction unit 53, the memory 54, the signal processing unit 55, the image storage unit 56, the image storage control unit 61, the display control unit 57, and the video signal generation unit 58, which are included in the processor device 16, are various processors to be described below. The various processors include, for example, a central processing unit (CPU) which is a general-purpose processor that executes software (programs) to function as various processing units, a programmable logic device (PLD) which is a processor having a changeable circuit configuration after manufacture, such as a field programmable gate array (FPGA), and a dedicated electrical circuit which is a processor having a dedicated circuit configuration designed to execute various processing.

One processing unit may be composed of one of these various processors or a combination of two or more of the processors of the same type or different types (for example, a plurality of FPGAs, or a combination of a CPU and an FPGA). Alternatively, a plurality of processing units may be composed of one processor. A first example in which a plurality of processing units are composed of one processor is an aspect in which one or more CPUs and software are combined to constitute one processor and the processor functions as a plurality of processing units, as typified by a computer such as a client or a server. A second example is an aspect in which a processor that realizes all of the functions of a system including a plurality of processing units with one integrated circuit (IC) chip is used, as typified by a system on chip (SoC) or the like. As described above, various processing units may be formed of one or more of the above various processors as hardware structures.

More specifically, the hardware structure of these various processors is an electrical circuit (circuitry) in which circuit elements, such as semiconductor elements, are combined.

EXPLANATION OF REFERENCES

10: endoscope system
12: endoscope
12a: insertion part
12b: operation part
12c: bendable portion
12d: distal end portion
12e: angle knob
12f: still image acquisition instruction portion
12g: mode changeover switch
12h: zoom operation portion 14: light source device
16: processor device
18: display
19: keyboard
20: light source unit
20a: V-LED
20b: B-LED
20c: G-LED
20d: R-LED
21: light source processor
22: light emission period setting unit
30a: illumination optical system
30b: image pickup optical system
41: light guide
42: illumination lens
43: objective lens
44: zoom lens
45: image pickup sensor
46: CDS/AGC circuit
47: A/D converter
51: image signal acquisition unit
52: DSP
53: noise reduction unit
54: memory
55: signal processing unit
56: image storage unit
57: display control unit
58: video signal generation unit
61: image storage control unit
62: central control unit
71, 74: first illumination light emission period
72, 73: second illumination light emission period
81a, 81b: slide bar
82a, 82b: slider
91, 92, 97, 98: period
93: still image acquisition instruction
94: predetermined period
95: second image
96: first image
BM: background mucous membrane
VS1: superficial blood vessel
VS2: deep blood vessel
VP: violet light image
GRP: green and red light image
ST110 to ST200: step

What is claimed is:

1. An endoscope system comprising:
a plurality of semiconductor light sources that emit light beams having wavelength bands different from each other;
a light source processor that is configured to:
  cause emission of a first illumination light beam during a first emission period of a cycle, the first illumination light beam having a first combination of light intensity ratios between the plurality of semiconductor light sources, and
  cause emission of a second illumination light beam during a second emission period of the cycle, the second illumination light beam having a second combination of light intensity ratios between the plurality of semiconductor light sources different from the first combination of light intensity ratios; and
an image processor,
wherein
the light source processor is further configured to cause emission of the first illumination light beam and the second illumination light beam during each of a first period and a second period,
the first period includes a plurality of consecutive cycles,
a number of the first emission periods exceeds a number of the second emission periods in each of the cycles in the first period such that the first illumination light beam is emitted for a longer duration than the second illumination light beam during the first period,
each of the cycles in the first period includes at least one of the first emission periods and at least one of the second emission periods,
the second period includes a plurality of consecutive cycles,
a number of the second emission periods exceeds a number of the first emission periods in each of the cycles in the second period such that the second illumination light beam is emitted for a longer duration than the first illumination light beam during the second period,
each of the cycles in the second period includes at least one of the first emission periods and at least one of the second emission periods, and
the image processor is configured to:
  acquire a plurality of first images obtained by imaging an observation target illuminated with the first illumination light beam during the first period,
  acquire a plurality of second images obtained by imaging the observation target illuminated with the second illumination light beam during the second period,
  perform image storage processing of storing the plurality of first images and the plurality of second images, and
  select and store at least one first image of the plurality of first images and at least one second image of the plurality of second images that satisfy a preset selection condition.

2. The endoscope system according to claim 1, wherein the selection condition is that a first image and a second image having least blur, out of the plurality of first images and the plurality of second images, are selected.

3. The endoscope system according to claim 1, wherein the selection condition is that a first image and a second image having a smallest positional deviation between the first image and the second image selected from the plurality of first images and the plurality of second images are selected.

4. The endoscope system according to claim 1, wherein the selection condition is that a first image and a second image having a smallest difference in acquisition time between the first image and the second image selected from the plurality of first images and the plurality of second images are selected.

5. The endoscope system according to claim 1, wherein the image processor is configured to cause display of the at least one first image and/or the at least one second image, on a display, and
display at least the at least one second image on the display during a display period.

6. The endoscope system according to claim 1, wherein the image processor is configured to cause display of the at least one first image and/or the at least one second image, on a display, and display at least the at least one first image on the display during a display period.

7. The endoscope system according to claim 1,
wherein the semiconductor light sources include a first semiconductor light source that emits a first narrow-band light beam having a wavelength band of which a central wavelength is 410±10 nm and a wavelength range is 380 to 420 nm, and a second semiconductor light source that emits a second narrow-band light beam having a wavelength band of which a central wavelength is 450±10 nm and a wavelength range is 420 to 500 nm.

8. The endoscope system according to claim 1,
wherein the image processor is configured to store the at least one first image and the at least one second image after adding information regarding the illumination light beams used.

9. The endoscope system according to claim 1, wherein the image processor is further configured to:
perform control to display the at least one first image and/or the at least one second image, on a display, and
perform control to display only the at least one first image on the display during the first period.

10. A method of operating an endoscope system including a plurality of semiconductor light sources that emit light beams having wavelength bands different from each other,
a light source processor configured to cause emission of a first illumination light beam during a first emission period of a cycle, the first illumination light beam having a first combination of light intensity ratios between the plurality of semiconductor light sources, and cause emission of a second illumination light beam during a second emission period of the cycle, the second illumination light beam having a second combination of light intensity ratios between the plurality of semiconductor light sources different from the first combination of light intensity ratios, and
an image processor, the method comprising:
causing, by the light source processor, emission of the first illumination light beam and the second illumination light beam during each of a first period and a second period,
wherein the first period includes a plurality of consecutive cycles,
a number of the first emission periods exceeds a number of the second emission periods in each of the cycles in the first period such that the first illumination light beam is emitted for a longer duration than the second illumination light beam during the first period,
each of the cycles in the first period includes at least one of the first emission periods and at least one of the second emission periods,
the second period includes a plurality of consecutive cycles,
a number of the second emission periods exceeds a number of the first emission periods in each of the cycles in the second period such that the second illumination light beam is emitted for a longer duration than the first illumination light beam during the second period, and
each of the cycles in the second period includes at least one of the first emission periods and at least one of the second emission periods;
acquiring, by the image processor, a plurality of first images obtained by imaging an observation target illuminated with the first illumination light beam during the first period;
acquiring, by the image processor, a plurality of second images obtained by imaging the observation target illuminated with the second illumination light beam during the second period;
performing, by the image processor, image storage processing of storing the plurality of first images and the plurality of second images; and
selecting and storing, by the image processor, at least one first image of the plurality of first images and at least one second image of the plurality of second images that satisfy a preset selection condition.

11. The method according to claim 10, further comprising:
performing, by the image processor, control to display the at least one first image and/or the at least one second image, on a display, and
performing, by the image processor, control to display only the at least one first image on the display during the first period.

* * * * *